US012767990B2

(12) United States Patent
Ventelä et al.

(10) Patent No.: US 12,767,990 B2
(45) Date of Patent: Oct. 20, 2026

(54) EPLIN AS A BIOMARKER FOR CANCER

(71) Applicant: Thestra Oy, Turku (FI)

(72) Inventors: Sami Ventelä, Turku (FI); Jukka Westermarck, Turku (FI)

(73) Assignee: Thestra Oy, Turku (FI)

( * ) Notice: Subject to any disclaimer, the term of this patent is extended or adjusted under 35 U.S.C. 154(b) by 895 days.

(21) Appl. No.: 17/917,902

(22) PCT Filed: Apr. 9, 2021

(86) PCT No.: PCT/FI2021/050260
§ 371 (c)(1),
(2) Date: Oct. 7, 2022

(87) PCT Pub. No.: WO2021/205078
PCT Pub. Date: Oct. 14, 2021

(65) Prior Publication Data

US 2023/0136717 A1 May 4, 2023

(30) Foreign Application Priority Data

Apr. 9, 2020 (FI) ..................................... 20205381

(51) Int. Cl.
*C12Q 1/6886* (2018.01)
*G01N 33/575* (2026.01)
*G01N 33/57515* (2026.01)
*G01N 33/57535* (2026.01)

(52) U.S. Cl.
CPC ..... *C12Q 1/6886* (2013.01); *G01N 33/57515* (2026.01); *G01N 33/57535* (2026.01); *G01N 33/57557* (2026.01); *G01N 33/57595* (2026.01); *C12Q 2600/106* (2013.01); *C12Q 2600/118* (2013.01); *C12Q 2600/158* (2013.01)

(58) Field of Classification Search
CPC ........................ C12Q 1/6886; C12Q 2600/106
See application file for complete search history.

(56) References Cited

U.S. PATENT DOCUMENTS

| | | | | |
|---|---|---|---|---|
| 2004/0058320 A1 | | 3/2004 | Roninson et al. | |
| 2005/0043907 A1 | | 2/2005 | Eckel et al. | |
| 2012/0302572 A1* | | 11/2012 | Kan ........................ | A61P 43/00 514/249 |

FOREIGN PATENT DOCUMENTS

| | | | |
|---|---|---|---|
| WO | 01/18019 | 3/2001 | |
| WO | 2008/051374 | 5/2008 | |
| WO | 2008/095050 | 8/2008 | |
| WO | WO-2008095050 A1 * | 8/2008 | ....... G01N 33/57492 |
| WO | 2009/065044 | 5/2009 | |
| WO | 2013/098797 | 7/2013 | |
| WO | 2019/032525 | 2/2019 | |

OTHER PUBLICATIONS

Liu et al. Anticancer Research. 2012. 32:1283-1290. (Year: 2012).*
Jiang et al. Molecular Cancer. 2008. 7:71, 10 pages. (Year: 2008).*
Zhang et al. Oncogene. 2011. 30:4941-4952. (Year: 2011).*
Whitehead et al. Genome Biology. 2005. 6:R13. (Year: 2005).*
Saito-Hisaminato et al. DNA Research. 2002. 9:35-45. (Year: 2002).*
Palmer et al. BMC Genomics. 2006. 7:115. (Year: 2006).*
Min et al. BMC Genomics. 2010. 11:96. (Year: 2010).*
Guillaume Jacquemet et al., "L-type calcium channels regulate filopodia stability and cancer cell invasion downstream of integrin signalling", Nature Communications, 7: 13297, Dec. 2016, pp. 1-17. https://doi.org/10.1038/ncomms13297.
Tatiana Lepikhova et al., "Drug-Sensitivity Screening and Genomic Characterization of 45 HPV-Negative Head and Neck Carcinoma Cell Lines for Novel Biomarkers of Drug Efficacy", Molecular Cancer Therapeutics 17(9), Sep. 2018, pp. 2060-2071. doi: 10.1158/1535-7163.MCT-17-0733.
Muna Taha et al., "EPLIN-α and -β Isoforms Modulate Endothelial Cell Dynamics through a Spatiotemporally Differentiated Interaction with Actin", Cell Reports 29, Oct. 2019, pp. 1010-1026. doi: 10.1016/j.celrep.2019.09.043.
International Search Report and Written Opinion of the ISA dated Jul. 12, 2021, for PCT/FI2021/050260, 16 pp.
Finnish Search Report dated Jul. 16, 2020, for FI 20205381, 2 pp.
Wen G. Jiang et al., "Eplin-alpha expression in human breast cancer, the impact on cellular migration and clinical outcome", Molecular Cancer, vol. 7, No. 1, Sep. 16, 2008, 10 pp.
Andrew J. Sanders et al., "EPLIN is a Negative Regulator of Prostate Cancer Growth and Invasion", The Journal of Urology, vol. 186, No. 1, Jul. 1, 2001, pp. 295-301.
Shumin Zhang et al., "EPLIN Downregulation Promotes Epithelial-Mesenchymal Transition in Prostate Cancer Cells and Correlates With Clinical Lymph Node Metastasis", Oncogene, vol. 30, No. 50, Dec. 1, 2011, 23 pp.
Rong Liu et al., "Epithelial protein lost in neoplasm-α (EPLIN-α) is a potential prognostic marker for the progression of epithelial ovarian cancer", International Journal of Oncology, vol. 48, No. 6, 2016, pp. 2488-2496.
Ross J. Collins et al., "Mechanistic insights of epithelial protein lost in neoplasm in prostate cancer metastasis", International Journal of Cancer, vol. 143, No. 10, Sep. 19, 2018, pp. 2537-2550.
Tomoko Ohashi et al., "p53 mediates the suppression of cancer cell invasion by inducing LIMA1/EPLIN", Cancer Letters, vol. 390, Apr. 1, 2017, pp. 58-66.
Yinan Liu et al., "EPLIN-α Expression in Human Oesophageal Cancer and its Impact on Cellular Aggressiveness and Clinical Outcome", Anticancer Research, vol. 32, 2012, pp. 1283-1290.

* cited by examiner

*Primary Examiner* — Joseph G. Dauner
(74) *Attorney, Agent, or Firm* — Nixon & Vanderhye PC

(57) ABSTRACT

The present invention relates to EPLIN as a biomarker for cancer and particularly small-size (T1/T2N0 and/or stage I/II) cancer. Thus, the invention provides use of EPLIN and an in vitro method of prognosing cancer or diagnosing aggressive cancer in a subject on the basis of the expression level of EPLIN. Also provided is a method for selecting treatment for cancer or predicting response to treatment. Also provided is a kit for use in said methods.

9 Claims, 8 Drawing Sheets

A

| Accession | Description | Found in Sample |
|---|---|---|
| **Q9UHB6** | **LIM domain and actin-binding protein 1 OS=Homo sapiens OX=9606 GN=LIMA1 PE=1 SV=1** | **High** |
| P14618 | Pyruvate kinase PKM OS=Homo sapiens OX=9606 GN=PKM PE=1 SV=4 | High |
| P00558 | Phosphoglycerate kinase 1 OS=Homo sapiens OX=9606 GN=PGK1 PE=1 SV=3 | High |
| **P00533** | **Epidermal growth factor receptor OS=Homo sapiens OX=9606 GN=EGFR PE=1 SV=2** | **High** |
| P60953 | Cell division control protein 42 homolog OS=Homo sapiens OX=9606 GN=CDC42 PE=1 SV=2 | High |
| P54819 | Adenylate kinase 2, mitochondrial OS=Homo sapiens OX=9606 GN=AK2 PE=1 SV=2 | High |
| P35579 | Myosin-9 OS=Homo sapiens OX=9606 GN=MYH9 PE=1 SV=4 | High |
| O00151 | PDZ and LIM domain protein 1 OS=Homo sapiens OX=9606 GN=PDLIM1 PE=1 SV=4 | High |

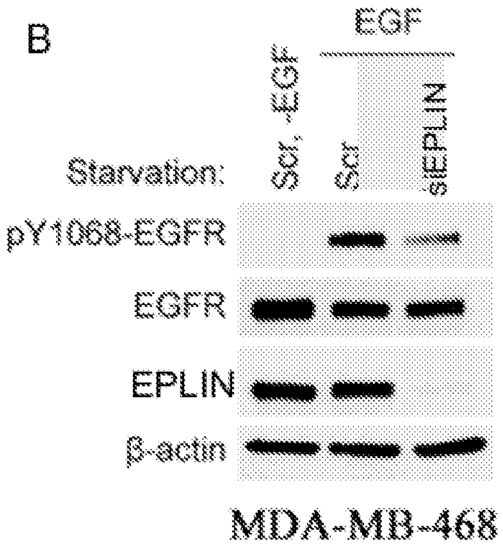

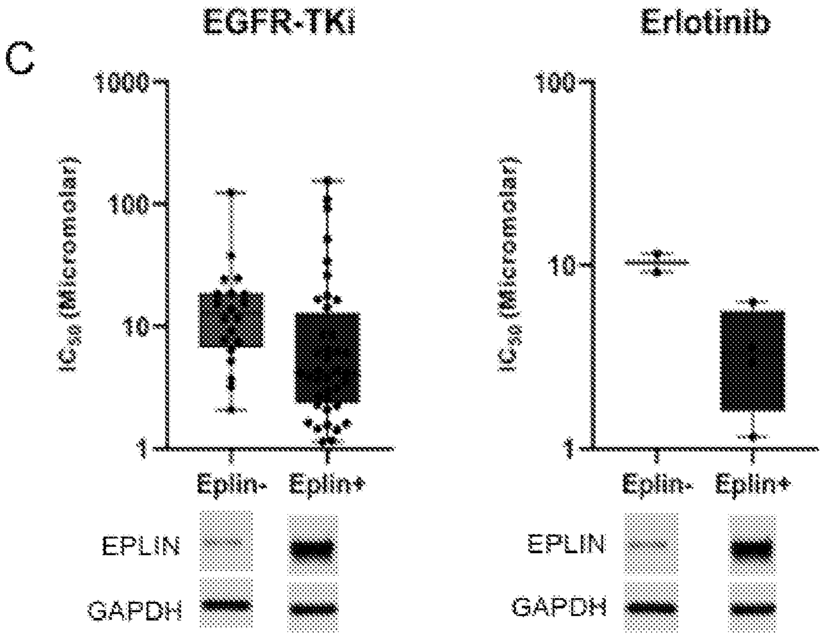

Figure 6

EPLIN AS A BIOMARKER FOR CANCER

CROSS-REFERENCE TO RELATED APPLICATION(S)

This application is the U.S. national phase of International Application No. PCT/FI2021/050260 filed Apr. 9, 2021, which designated the U.S. and claims priority to FI 20205381 filed Apr. 9, 2020, the entire contents of each of which are hereby incorporated by reference.

FIELD OF THE INVENTION

The invention relates to biomarkers and methods for diagnosing aggressiveness of cancer or prognosing the outcome of cancer.

BACKGROUND OF THE INVENTION

Cancer affects tens of millions of human and animal individuals yearly and is among the leading causes of death globally. Recurrent and/or metastatic cancer is characterized by a poor prognosis, and there is an unmet need for the development of biomarkers for accurately providing a prognosis. A type of cancer, head and neck squamous cell carcinoma (HNSCC) develops in the mucous membranes of the oral cavity, oropharynx, nasal cavity and paranasal sinuses, naso-pharynx, larynx and hypopharynx. HNSCC constitutes approximately 4% of all cancers worldwide. HNSCC is traditionally associated with tobacco and alcohol consumption, and a growing proportion of head and neck tumors, mainly of the oropharynx, are associated with Human Papilloma Virus (HPV).

A further clinical problem in the treatment of cancer patients is the diagnosis and prognosis of small-size tumors (T1/T2N0 in TNM staging and/or stage I/II in overall stage grouping). Because of their small size and presumedly non-aggressive nature, many of these tumors are typically treated with mono-therapy i.e. conventional surgery. Unfortunately, for example an estimated 20% to 50% among small-size (T1/T2N0) HNSCC tumors represent aggressively behaving cancers, suggesting that these patients have features in their primary tumors causing aggressive behaviour. At the moment there is no clinically accepted biomarker available to distinguish these aggressively behaving cancers from the local, non-aggressive forms of cancer. Such a biomarker could also be used in selecting appropriate therapy according to aggressiveness of cancer. Based on a diagnosis of cancer aggressiveness, more intense therapy may be selected for patients diagnosed with aggressive cancer than for patients with non-aggressive cancer.

Thus, there is a longstanding need for biomarkers for providing a prognosis for cancer, diagnosing aggressively behaving cancer as well as selecting appropriate therapies for the treatment of primary tumor and possible metastases.

BRIEF DESCRIPTION OF THE INVENTION

An object of the present invention is to provide methods, protein profiles and kits useful for diagnosing and prognosing cancer in a subject as well as selecting treatment for a subject with cancer. The object of the invention is achieved by what is stated in the independent claims. The embodiments of the invention are disclosed in the dependent claims.

At least some embodiments of the invention are based on the evaluation of patient samples in order to identify novel molecular markers that accurately determine cancer patient outcomes upon initial diagnosis. It was surprisingly found that determining expression of EPLIN protein provides diagnosis of aggressiveness of cancer or prognosis of the cancer.

Thus, in one aspect, the invention provides a method of diagnosing aggressiveness of cancer in a subject diagnosed with cancer, comprising assaying a sample obtained from said subject for expression level of EPLIN, comparing the assayed expression level of EPLIN to a control level, and providing a diagnosis of aggressiveness the basis of said comparison. In a further aspect, the method of diagnosing aggressiveness of cancer further comprises selecting treatment to the subject on the basis of said comparison.

In another aspect, the invention provides a method of providing prognosis of cancer in a subject, comprising assaying a sample obtained from said subject for expression level of EPLIN, comparing the assayed expression level of EPLIN to a control level, and providing a prognosis of cancer on the basis of said comparison.

In a further aspect of the invention, the cancer is a small-size (i.e. T1/T2N0 and/or stage I/II) cancer. The method thus provides a diagnosis of aggressiveness or a prognosis of a small-size cancer in a subject.

In still another aspect, the invention provides use of EPLIN as a biomarker for providing a prognosis of cancer or determining diagnosis of aggressive cancer.

In a yet further aspect, the invention provides use of a kit comprising one or more reagents that specifically detect EPLIN for providing a prognosis of cancer or diagnosing aggressiveness of cancer.

In yet another aspect of the invention, the cancer is head and neck squamous cell carcinoma (HNSCC), breast cancer (BC), colorectal cancer (CRC) or bladder cancer. The invention thus provides a method for prognosis of HNSCC, BC, CRC or bladder cancer, or diagnosis of aggressiveness of HNSCC, BC, CRC or bladder cancer in a subject.

In a still further aspect of the invention, EPLIN is assayed as expression level of total EPLIN, EPLIN alpha or EPLIN beta or any combination thereof. In this aspect, the methods, uses and kits of the invention thus comprise determining expression level of total EPLIN, EPLIN alpha or EPLIN beta or any combination thereof. Also, in this aspect, the kit of the invention comprises one or more reagents that specifically detect total EPLIN, EPLIN alpha or EPLIN beta or any combination thereof.

Objects, aspects, embodiments, details and advantages of the present invention will become apparent from the following figures, detailed description, examples, and claims.

BRIEF DESCRIPTION OF THE DRAWINGS

In the following the invention will be described in greater detail by means of embodiments with reference to the accompanying drawings, in which

FIG. 4A illustrates the results of siRNA silencing of EPLIN ('siLIMA1'). Depletion of EPLIN slowed cell migration in UT-SCC-14 and UT-SCC-60B cells. FIG. 4B shows examination of cell invasive ability in different head and neck cancer cell lines. FIG. 4C shows depletion of LIMA1 inhibited cell invasion in UT-SCC-14, UT-SCC-45 and UT-SCC-60B HNSCC cells.

FIG. 6A shows the results of a mass spectrometry analysis indicating that EPLIN protein (LIMA1) interacts strongly with epidermal growth factor receptor (EGFR) protein. FIG. 6B illustrates results of silencing EPLIN (siEPLIN), leading to reduction of activity of EGFR protein after epidermal growth factor (EGF) stimulation in the breast cancer cell line MDA-MB-468. As illustrated in FIG. 6C, silencing EPLIN also decreases the sensitivity of HNSCC cell lines to EGFR tyrosine kinase inhibitors ('EGFR-TKi'). The tested EGFR-TKis were the EGFR inhibitor (EGFRi) drugs Erlotinib, AZD9291, Afatinib, Cetuximab, AZD8931, Gefitinib and Neratinib. Of the tested EGFRis, Erlotinib had the strongest effect as shown in FIG. 6C.

DETAILED DESCRIPTION OF THE INVENTION

Figure 1A:
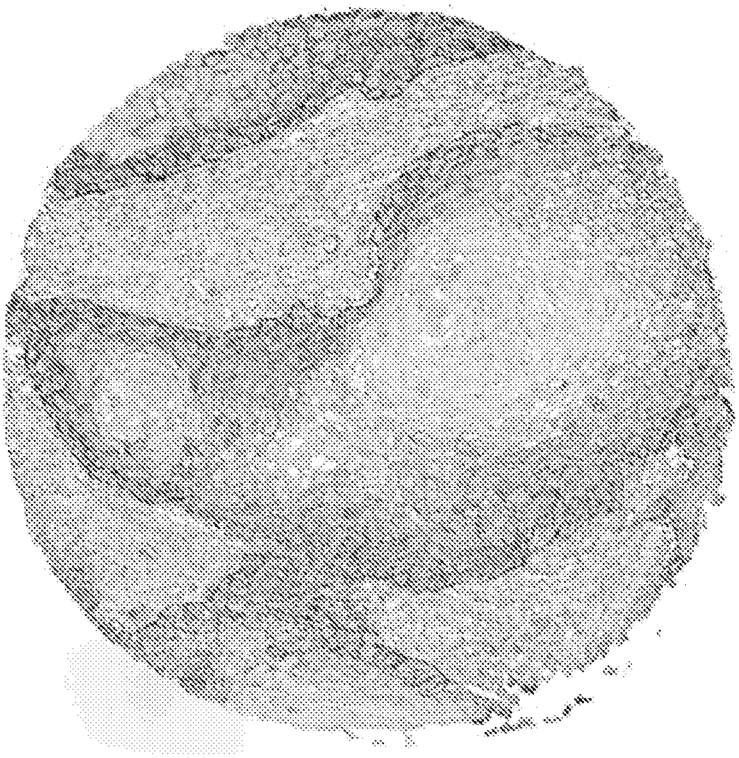
FIG. 1 illustrates LIMA-1/EPLIN expression in HNSCC. A) An immunohistochemical staining of HNSCC exhibiting increased EPLIN expression. EPLIN expression is prominently located in the so-called invasive front of the tumor. B) An immunohistochemical staining of HNSCC exhibiting non-increased EPLIN expression. C) and D) In small-size HNSCC tumors T1/T2N0 (C) and stage I/II (D), strong LIMA-1/EPLIN expression is associated with significantly worse life survival as compared to HNSCC patients with low LIMA-1/EPLIN expression in HNSCC. E) Western blot analysis from fresh HNSCC cancer samples (Tumor), normal tissue samples (Norm) and HNSCC cancer cell lines (UT-SCC). Tumor size (T) and metastasis to local lymph nodes (N) of HNSCC patients are indicated above the patients' Western blot analyzes.

The present invention is based on identification of EPLIN as a biomarker for various aspects of cancer. Accordingly, herein is provided use of EPLIN and an in vitro method of determining the outcome of cancer in a subject on the basis of expression level of EPLIN in a sample obtained from said subject. More specifically, said method may be formulated e.g. as an in vitro method of diagnosing aggressiveness of cancer in a subject diagnosed with cancer, wherein the method comprises or consists of assaying a sample obtained from said subject for expression level of EPLIN, comparing the assayed expression level of EPLIN to a control level, and providing a diagnosis of aggressiveness of cancer on the basis of said comparison. Alternatively, said method may be formulated e.g. as a method of determining prognosis of cancer in a subject, wherein the method comprises or consists of assaying a sample obtained from said subject for expression level of EPLIN, comparing the assayed expression level of EPLIN to a control level, and providing a prognosis of cancer on the basis of said comparison.

The expression level of EPLIN correlates with the probable outcome of cancer such that increased expression level of EPLIN as compared with a control expression level is indicative of aggressive cancer or poor prognosis such as reduced overall survival. On the other hand, a non-increased or decreased expression of EPLIN is indicative of non-aggressive cancer or good prognosis such as non-reduced overall survival. The cancer to be diagnosed or prognosed may be all types of cancer tumors to develop personalized medicine and assist in deciding whether a patient may need more extensive surgical and/or oncological treatment modalities for the cancer disease to achieve better cancer survival.

In an aspect of the invention the cancer is one or more cancer(s) selected from head and neck cancers including different histological subtypes (i.e. squamous cell carcinomas, salivary gland carcinomas, mucosal melanoma); skin cancers including different histological subtypes (squamous cell carcinoma, basal cell carcinoma, melanoma); breast cancer; gastrointestinal cancers including different histological subtypes locating in oesophagus, stomach, small intestine, large intestine, rectum and anus; gynaecological cancers including different histological subtypes locating in cervix, ovary, uterine, vagina and vulva; urogenital cancers including different histological subtypes locating in the prostate, kidney, bladder and testicle and/or brain cancers. In a further aspect, the cancer is head and neck squamous cell carcinoma (HNSCC), breast cancer (BC), colorectal cancer (CRC) or bladder cancer.

In an aspect of the invention, the cancer to be diagnosed or prognosed is small-size cancer which is T1/T2N0 in TNM staging and/or stage I/II in overall stage grouping.

In a further aspect, the invention provides the use of EPLIN as a biomarker for diagnosing aggressiveness of cancer or for determining prognosis of cancer in a subject in need thereof. Instead of "diagnosing aggressiveness" or "diagnosing" and the like, the term "determining aggressiveness" and "determining" and the like may be employed in all aspects of the invention.

The expression level of EPLIN correlates with diagnosis of cancer tumors such that increased expression level of EPLIN as compared with a control level of expression in a control is indicative of aggressive cancer. On the other hand, a non-increased or decreased expression of EPLIN is indicative of non-aggressive cancer. The cancer tumor diagnosed for aggressiveness may be small-size (i.e. T1/T2N0 and/or stage I/II).

In all aspects and embodiments of the present invention the cancer may be HNSCC, breast cancer (BC), colorectal cancer (CRC) or bladder cancer. In the context of this application, the term "cancer" may refer to any of these cancers.

EPLIN or LIMA-1/EPLIN is epithelial protein lost in neoplasm (EPLIN) protein encoded by the LIM domain and actin binding 1 (LIMA-1) gene. In the context of this application, the terms "EPLIN", "LIMA-1", "LIMA1", "LIMA-1/EPLIN" and the like may be used interchangeably.

Two isoforms of EPLIN, EPLIN-α and EPLIN-β have been identified. Herein, the terms "EPLIN-α", "EPLIN alpha" and "LIMA-1/EPLIN alpha" and the like may be used interchangeably. Also herein, the terms "EPLIN-β", "EPLIN beta" and "LIMA-1/EPLIN beta" and the like may be used interchangeably.

The mRNA of the β isoform comprises all 11 exons of the LIMA-1/EPLIN transcript, whereas EPLIN-α mRNA only comprises exons 4-11. EPLIN-α protein has 600 amino acid (aa) residues and EPLIN-β is extended by an additional 160 aa. Both isoforms contain a single centrally located LIM domain that can form two closely spaced zinc-binding subdomains and allow EPLIN to dimerize or associate with other proteins. EPLIN also contains at least two actin-binding domains at both the amino and carboxyl termini.

EPLIN has been suggested to regulate actin cytoskeleton and cellular architecture via the two actin-binding domains which allow EPLIN to cross-link actin filaments, lower the monomer dissociation rate constant and stabilize from depolymerization. EPLIN also stabilizes the circumferential actin belt at adherens junctions by forming a cadherin-β-catenin-α-catenin-EPLIN-F-actin complex essential to the maintenance of apical-basal polarity in epithelial cells. EPLIN has also been suggested to have a role in the regulation of cytokinesis and in cell adhesion.

EPLIN has also been indicated as a tumor suppressor in cancers. Increased expression or ectopic expression of EPLIN has been associated with suppressing growth of osteosarcoma, breast cancer, prostate cancer and esophageal cancer cells or tumors. On the other hand, EPLIN depletion i.e. decreased expression has been shown to increase growth and/or invasiveness of ovarian, breast, prostate, HNSCC and melanoma cancer cells. EPLIN has also been determined to be downregulated in certain human cancer cell lines and primary tumors.

Previous and recent publications have shown somewhat conflicting results in relation to the roles of LIMA-1/EPLIN in cancer biology. This may be due to the two different isoforms of EPLIN which may have different roles in cells. A recent publication suggests that EPLIN-α controls protrusion dynamics in growing and migrating endothelial cells, while EPLIN-β has an actin filament stabilizing role (Taha et al., 2019). However, particular roles of EPLIN alpha and beta isoforms have until now been unclear in cancer.

As used herein, the term "or" has the meaning of both "and'" and "or" (i.e. "and/or"). Furthermore, the meaning of a singular noun includes that of a plural noun and thus a singular term, unless otherwise specified, may also carry the meaning of its plural form. In other words, the term "a" or "an" may mean one or more.

As used herein, the terms "biomarker" and "marker" are interchangeable, and refer to a molecule which is differentially present in a sample taken from cancerous tissue of a subject with cancer as compared to a sample taken from noncancerous, healthy tissue of the same subject or a comparable sample take from a control subject, such as an apparently healthy i.e. non-diseased subject or a subject with the same cancer but having a different prognosis or diagnosis of aggressiveness of the disease.

As used herein, the term "determining an expression level of EPLIN", and any corresponding expressions, refer to quantifying or semi-quantifying EPLIN either on the basis of mRNA, cDNA, or protein amount. The term "level" is interchangeable with the terms "amount" and "concentration", and can refer to an absolute or relative quantity. Determining EPLIN expression may also include determining the absence or presence of EPLIN qualitatively for example by a Western blot or a tissue/cell stain.

To make any conclusions on the basis of EPLIN expression level, it may be compared with a control level. Once the control level is known, the determined or detected EPLIN expression level can be compared therewith and the significance of the difference can be assessed using standard statistical methods.

In some embodiments, a statistically significant difference between the determined EPLIN level and the control level is indicative of a certain prognosis, such as poor prognosis that may manifest itself e.g. as reduced overall survival or reduced relapse-free survival, or good prognosis that may manifest itself e.g. as increased overall survival or increased relapse-free survival. In some other embodiments, a statistically significant difference between the determined EPLIN level and the control level is indicative of aggressive or non-aggressive cancer, or of positive or negative response to treatment of cancer. In some further embodiments, before being compared with the control, the EPLIN levels are normalized using standard methods.

As used herein, the term "control" may refer to many different types of controls. For example, "negative control" or "normal control" may mean a non-cancerous tissue of the same subject, or a sample obtained from an apparently healthy i.e. non-diseased individual or a pool of apparently healthy i.e. non-diseased individuals, from which the expression level of EPLIN, alone or in comparison with another marker, is determined to obtain a control level. "Positive control" may mean, for example, cancerous tissue of the same subject, or a sample obtained from an individual diagnosed with cancer, or a pool of individuals diagnosed with cancer from which the expression level of EPLIN, alone or in comparison with another marker, is determined to obtain a control level. A predetermined threshold value that is indicative of a given diagnosis or prognosis may also be employed as a control, i.e. "threshold control". Accordingly, the threshold value may be a negative control value obtained from a pool of apparently healthy individuals, wherein the value refers to expression levels of EPLIN in normal, non-cancerous cells; or it may be a positive control value, obtained from a pool of individuals with cancer, wherein the value refers to an expression level of EPLIN in cancerous tissues. A "control level" is an expression level of EPLIN, alone or in comparison with another marker, determined from any control described herein.

In some embodiments, such as those relating to predicting response to treatment or monitoring purposes, such as monitoring for a minimal residual disease, "threshold control" refers to an expression level of EPLIN in a sample obtained from the same subject at a different time point, such as at the time of diagnosis or before the treatment for cancer or at the time when patient has achieved clinical remission.

"Internal control" may refer to an expression level of one or more appropriate housekeeping genes determined from the same cells as the expression level of EPLIN. In other words, the internal control may mean a loading control which allows quantifying EPLIN in the sample being analysed. Examples for an internal control, in other words "loading control" or "quantifying control" include housekeeping genes and housekeeping proteins. The quantity of EPLIN may also be measured relative to another cancer biomarker, such as a known HNSCC biomarker (e.g. p16 and PD-L1), which in this context may be denoted as "control biomarker". "Control ratio" means the relationship of EPLIN to any selected control, for example the ratio between EPLIN and a control biomarker.

Thus, in some embodiments, the expression level of EPLIN may be determined as a relative ratio between the expression level of EPLIN and that of an appropriate housekeeping gene in the same cells. Non-limiting examples of suitable housekeeping genes include GAPDH (Glyceraldehyde-3-phosphate dehydrogenase), ABL1 (ABL proto-oncogene 1), ACTB (Actin, beta), RRN18S (18S ribosomal RNA), PGK1 (Phosphoglycerate kinase 1), PPIA (Peptidyl-prolyl isomerase A (cyclophilin A)), RPL13A (Ribosomal protein L13a), RPLP0 (Ribosomal protein, large, P0), B2M (Beta-2-microglobulin), YWHAZ (Tyrosine 3-monooxygenase/tryptophan 5-monooxygenase activation protein, zeta polypeptide), SDHA (Succinate dehydrogenase), TFRC (Transferrin receptor (p90, CD71)), ALAS1 (Amino-levulinate, delta-, synthase 1), GUSB (Glucuronidase, beta), HMBS (Hydroxy-methyl-bilane synthase), HPRT1 (Hypoxanthine phosphoribosyltransferase 1), TBP (TATA box binding protein), and TUBB (Tubulin, beta polypeptide). In some embodiments, preferred housekeeping genes include GAPDH and ACTB.

Statistical methods for determining appropriate control levels or threshold values will be readily apparent to those of ordinary skill in the art. The control levels or threshold values may have been determined, if necessary, from controls that are samples of subjects of the same age group, demographic features, and/or disease status, etc. The negative control level or threshold value may originate from a single individual not affected by a cancer in question or a subtype thereof, or be pooled from more than one such individual.

As used herein, the term “increased expression” refers to an increase in the amount of a biomarker such as EPLIN in a sample as compared with a control level. Said increase can be determined qualitatively and/or quantitatively according to standard methods known in the art. The expression is increased if the amount or level of the biomarker in the sample is, for instance, at least about 1.5 times, 1.75 times, 2 times, 3 times, 4 times, 5 times, 6 times, 8 times, 9 times, time times, 10 times, 20 times or 30 times the control value or the amount of the same biomarker in the control. In some embodiments, the term “increased expression” refers to a statistically significant increase in the level or amount of the biomarker as compared with that of a control, preferably negative control. Increased expression as compared with a negative control may indicate that the subject has or is at increased risk of having e.g. poor prognosis or aggressive cancer or negative response to treatment.

As used herein, the term “non-increased expression” refers to an expression level of a biomarker such as EPLIN that is essentially the same both in a sample to be analysed and in a control. In some embodiments, non-increased expression as compared to a negative control indicates that the subject does not have or is not at risk of having e.g. poor prognosis or aggressive cancer or positive response to treatment. On the other hand, corresponding expression level as compared to a positive control indicates that the subject is at risk of having e.g. poor prognosis or aggressive cancer or negative response to treatment.

As used herein, the term “decreased expression” refers to a decrease in the amount of a biomarker such as EPLIN in a sample as compared with a control level. Said decrease can be determined qualitatively and/or quantitatively according to standard methods known in the art. The expression is decreased if the amount or level of the biomarker in the sample is, for instance, at least about 1.5 times, 1.75 times, 2 times, 3 times, 4 times, 5 times, 6 times, 8 times, 9 times, 10 times, 20 times or 30 times lower that the control value or the amount of the same biomarker in the control. In some embodiments, the term “decreased expression” refers to a statistically significant decrease in the level or amount of the biomarker as compared with that of a control. Decreased expression as compared with a positive control may indicate that the subject does not have or is not at risk of having e.g. poor prognosis or aggressive cancer, or negative response to treatment.

As used herein, the term “sample” refers to a biological or clinical sample obtained from a subject whose EPLIN expression level is to be determined. Preferred sample types include tumor samples obtained e.g. by a biopsy or aspiration, saliva, and blood samples, such as whole blood, serum and plasma.

The term “sample” also includes samples that have been manipulated or treated in any appropriate way after their procurement, including but not limited to centrifugation, filtration, precipitation, dialysis, chromatography, treatment with reagents, washing, or enriching for a certain component of the sample such as a cell population.

As used herein, the term “subject” refers to any mammal including, but not limited to, humans and domestic animals such as livestock, pets and sporting animals. Examples of such animals include without limitation carnivores such as cats and dogs and ungulates such as horses. Thus, the present invention may be applied in both human and veterinary medicine. As used herein, the terms “subject”, “patient” and “individual” are interchangeable.

As used herein, a subject “in need” of e.g. treatment or determining expression level of a biomarker or diagnosis or prognosis refers to a subject that has cancer or has been diagnosed with cancer, and is therefore in need of measures to e.g. determine expression level of a biomarker or to provide a prognosis of the cancer or a diagnosis of aggressiveness of the cancer or a treatment of the cancer.

As used herein, the term “apparently healthy” or “non-diseased” refers to an individual or a pool of individuals who show no signs of cancer such as HNSCC, breast cancer, colorectal cancer or bladder cancer, and thus are believed not to be affected by said cancer and/or who are prognosed not to develop said cancer.

As used herein, the term “prognosis” refers to a probable course or clinical outcome of a disease, while the expressions “prognosticating” and “prognosing” refer to a prediction of future course of the disease.

As used herein, the term “good prognosis” refers to a probable favourable course of the disease for a certain period of time. “Prolonged overall survival”, “prolonged disease-free survival”, “prolonged recurrence-free survival” and “prolonged progression-free survival”, when compared to the median outcome of the disease for example, are non-limiting examples of good prognosis. Depending on the cancer and embodiment in question, good prognosis may refer to, for example at least 20%, at least 30%, at least 40%, at least 50%, at least 60%, at least 70%, at least 80% or at least 90% chance of surviving more than 1 year, more than 2 years, more than 3 years, more than 4 years or more than 5 years after primary diagnosis.

As used herein, term “poor prognosis” refers to a probable non-favourable course of the disease for a certain period of time. “Reduced overall survival”, “reduced disease-free survival”, “reduced recurrence-free survival” and “reduced progression-free survival”, when compared to the median outcome of the disease for example, are non-limiting examples of poor prognosis. Depending on the cancer and embodiment in question, poor prognosis may refer to, for example less than 60%, less than 50%, less than 40%, less than 30%, less than 20% or less than 10% likelihood of surviving more than 1 year, more than 2 years, more than 3 years, more than 4 years or more than 5 years after primary diagnosis.

In summary, increased expression level of EPLIN may be an indicator of poor prognosis, such as reduced overall survival; whereas non-increased or decreased expression level of EPLIN may be an indicator of good prognosis, such as non-reduced or prolonged overall survival.

As used herein, the term "aggressive" in the expression aggressive cancer or aggressive HNSCC refers to a cancer that shows invasiveness i.e. exhibits direct extension and penetration by cancer cells into neighbouring tissues. Terms such "aggressive cancer" and "aggressive behaviour of cancer" and "aggressively behaving cancer" and the like may herein be used interchangeably. As a further non-limiting example, aggressive cancer is also metastatic i.e. shows spreading from a primary site to a different or secondary site within the host's body. For example, a small-size cancer tumor (T1/T2N0 and/or stage I/II) diagnosed or determined as aggressive based on EPLIN expression as described herein, is likely to progress to be staged as T3 or T4 in the TNM staging system or as an III stage or IV stage cancer in the overall stage grouping, and also through showing lymph node metastasis and/or distant metastasis beyond regional lymph nodes, to be staged as N1, N2 or N3 or M1 in the TNM staging. A cancer staged N0 is typically also stage M0 i.e. shows no distant metastasis. For example, in our retrospective HNSCC data concerning stage I-II HNSCC disease and our prospective HNSCC data concerning stage II-IV disease, increased EPLIN expression was associated with a dramatic decrease in survival rates within 1-2 years after diagnosis. The results suggest that increased intra- and/or extratumoral EPLIN expression is linked to active aggressive cancer which should be taken into consideration in cancer patient treatment planning. In addition, the findings presented herein show differentiation of invasive i.e. aggressive cancer from non-invasive cancer through determining EPLIN expression in HNSCC, bladder cancer and colorectal cancer samples. Also, silencing of EPLIN expression is presented herein to dramatically reduce invasiveness of HNSCC and breast cancer cell lines, strongly linking EPLIN expression to cancer aggressiveness.

Depending on the cancer and embodiment in question, aggressive cancer may refer to, for example more than 40%, more than 50%, more than 60%, more than 70%, more than 80% or more than 90% a likelihood of the cancer progressing beyond T1/T2N0 and/or stage I/II within 1 year, 2 years, 3 years, 4 years or 5 years after the primary diagnosis.

As a further non-limiting example, aggressive cancer may refer to a probable unfavourable course of the disease over time. "Reduced overall survival", "reduced disease-free survival", "reduced recurrence-free survival" and "reduced progression-free survival", when compared to the median outcome of the disease for example, are non-limiting examples of aggressive behaviour of cancer. Depending on the cancer and embodiment in question, aggressive cancer may refer to, for example less than 60%, less than 50%, less than 40%, less than 30%, less than 20% or less than 10% likelihood of surviving more than 1 year, more than 2 years, more than 3 years, more than 4 years or more than 5 years after the primary diagnosis.

As used herein, the term "non-aggressive" in the expression non-aggressive cancer refers to a cancer that does not show invasiveness i.e. does not exhibit direct extension and penetration by cancer cells into neighbouring tissues. Terms such "non-aggressive cancer" and "non-aggressive behaviour of cancer" and "non-aggressively behaving cancer" and the like may herein be used inter-changeably. As a further non-limiting example, non-aggressive cancer is also not metastatic i.e. does not show spreading from a primary site to a different or secondary site within the host's body. Thus, a non-aggressive cancer remains local and thus e.g. exhibits slow growth. A small-size cancer tumor (T1/T2N0 and/or stage I/II) diagnosed as non-aggressive based on negative or low EPLIN expression as described herein, is likely to not progress and thus remains staged as T1/T2N0 and/or stage I/II. The non-aggressive cancer may therefore be treated with monotherapy i.e. surgery only with sufficient surgical margins.

Depending on the cancer and embodiment in question, non-aggressive cancer may refer to, for example less than 60%, less than 50%, less than 40%, less than 30%, less than 20% or less than 10% a likelihood of the cancer progressing beyond T1/T2N0 and/or stage I/II within 1 year, 2 years, 3 years, 4 years or 5 years after the primary diagnosis.

As a further non-limiting example, non-aggressive cancer may refer to a probable favourable course of the disease over time. "Prolonged overall survival", "prolonged disease-free survival", "prolonged recurrence-free survival" and "prolonged progression-free survival", when compared to the median outcome of the disease for example, are non-limiting examples of non-aggressively behaving cancer. Depending on the cancer and embodiment in question, non-aggressive cancer may refer to, for example at least 20%, at least 30%, at least 40%, at least 50%, at least 60%, at least 70%, at least 80% or at least 90% chance of surviving more than 1 year, more than 2 years, more than 3 years, more than 4 years or more than 5 years after primary diagnosis.

In summary, increased expression level of EPLIN may be an indicator of aggressive cancer, such as a cancer showing invasiveness and/or reduced overall survival; whereas non-increased or decreased expression level of EPLIN may be an indicator of non-aggressive cancer, such as cancer showing no invasiveness and/or prolonged overall survival.

In an aspect of the invention, as used herein, in individuals with HNSCC, breast cancer, colorectal cancer or bladder cancer, the term "prognosis" refers to a probable course or clinical outcome of HNSCC, breast cancer, colorectal cancer or bladder cancer, while the expressions "prognosticating" and "prognosing" refer to a prediction of future course of the disease.

In an aspect of the invention, as used herein, the term "good prognosis" refers to a probable favourable course of HNSCC, breast cancer, colorectal cancer or bladder cancer for a certain period of time. "Prolonged overall survival", "prolonged disease-free survival", "prolonged recurrence-free survival" and "prolonged progression-free survival", when compared to the median outcome of HNSCC for example, are non-limiting examples of good prognosis. Depending on the embodiment in question, good prognosis may refer to, for example at least 20%, at least 30%, at least 40%, at least 50%, at least 60%, at least 70%, at least 80% or at least 90% chance of surviving more than 1 year, more than 2 years, more than 3 years, more than 4 years or more than 5 years after primary diagnosis of HNSCC.

In an aspect of the invention, as used herein, term "poor prognosis" refers to a probable non-favourable course of HNSCC, breast cancer, colorectal cancer or bladder cancer for a certain period of time. "Reduced overall survival", "reduced disease-free survival", "reduced recurrence-free survival" and "reduced progression-free survival", when compared to the median outcome of HNSCC, breast cancer, colorectal cancer or bladder cancer for example, are non-limiting examples of poor prognosis. Depending on the embodiment in question, poor prognosis may refer to, for example less than 60%, less than 50%, less than 40%, less than 30%, less than 20% or less than 10% likelihood of surviving more than 1 year, more than 2 years, more than 3 years, more than 4 years or more than 5 years after primary diagnosis of HNSCC, breast cancer, colorectal cancer or bladder cancer.

In an aspect of the invention, in summary, increased expression level of EPLIN may be an indicator of poor prognosis of HNSCC, breast cancer, colorectal cancer or bladder cancer, such as reduced overall survival; whereas non-increased or decreased expression level of EPLIN may be an indicator of good prognosis of HNSCC, breast cancer, colorectal cancer or bladder cancer, such as non-reduced or prolonged overall survival.

In an aspect of the invention, as used herein, the term "aggressive" in the expression aggressive HNSCC, breast cancer, colorectal cancer or bladder cancer refers to HNSCC, breast cancer, colorectal cancer or bladder cancer showing invasiveness i.e. exhibiting direct extension and penetration by cancer cells into neighbouring tissues. Terms such "aggressive HNSCC, breast cancer, colorectal cancer or bladder cancer" and "aggressive behaviour of HNSCC, breast cancer, colorectal cancer or bladder cancer" and "aggressively behaving HNSCC, breast cancer, colorectal cancer or bladder cancer" and the like may herein be used interchangeably. As a further non-limiting example, aggressive HNSCC, breast cancer, colorectal cancer or bladder cancer is also metastatic i.e. shows spreading from a primary site to a different or secondary site within the host's body. For example, a small-size HNSCC, breast cancer, colorectal cancer or bladder cancer tumor (T1/T2N0 and/or stage I/II) diagnosed as aggressive based on EPLIN expression as described herein, is likely to progress to be staged as T3 or T4 in the TNM staging system or as an III stage or IV stage HNSCC, breast cancer, colorectal cancer or bladder cancer in the overall stage grouping, and also through showing lymph node metastasis and/or distant metastasis beyond regional lymph nodes, to be staged as N1, N2 or N3 or M1 in the TNM staging. A HNSCC, breast cancer, colorectal cancer or bladder cancer staged N0 is typically also stage M0 i.e. shows no distant metastasis.

Depending on the HNSCC, breast cancer, colorectal cancer or bladder cancer and embodiment in question, aggressive HNSCC, breast cancer, colorectal cancer or bladder cancer may refer to, for example more than 40%, more than 50%, more than 60%, more than 70%, more than 80% or more than 90% a likelihood of the HNSCC, breast cancer, colorectal cancer or bladder cancer progressing beyond T1/T2N0 and/or stage I/II within 1 year, 2 years, 3 years, 4 years or 5 years after the primary diagnosis.

In an aspect of the invention, as a further non-limiting example, aggressive HNSCC, breast cancer, colorectal cancer or bladder cancer may refer to a probable unfavourable course of the disease over time. "Reduced overall survival", "reduced disease-free survival", "reduced recurrence-free survival" and "reduced progression-free survival", when compared to the median outcome of HNSCC, breast cancer, colorectal cancer or bladder cancer for example, are non-limiting examples of aggressive behaviour of cancer. Depending on the embodiment in question, aggressive HNSCC, breast cancer, colorectal cancer or bladder cancer may refer to, for example less than 60%, less than 50%, less than 40%, less than 30%, less than 20% or less than 10% likelihood of surviving more than 1 year, more than 2 years, more than 3 years, more than 4 years or more than 5 years after the primary diagnosis of HNSCC, breast cancer, colorectal cancer or bladder cancer.

In an aspect of the invention, as used herein, the term "non-aggressive" in the expression non-aggressive HNSCC, breast cancer, colorectal cancer or bladder cancer refers to a HNSCC, breast cancer, colorectal cancer or bladder cancer that does not show invasiveness i.e. does not exhibit direct extension and penetration by cancer cells into neighbouring tissues. Terms such "non-aggressive HNSCC, breast cancer, colorectal cancer or bladder cancer" and "non-aggressive behaviour of HNSCC, breast cancer, colorectal cancer or bladder cancer" and "non-aggressively behaving HNSCC, breast cancer, colorectal cancer or bladder cancer" and the like may herein be used interchangeably. As a further non-limiting example, non-aggressive HNSCC, breast cancer, colorectal cancer or bladder cancer is also not metastatic i.e. does not show spreading from a primary site to a different or secondary site within the host's body. Thus, a non-aggressive HNSCC, breast cancer, colorectal cancer or bladder cancer remains local and thus e.g. exhibits slow growth. A small-size HNSCC, breast cancer, colorectal cancer or bladder cancer tumor (T1/T2N0 and/or stage I/II) diagnosed as non-aggressive based on negative or low EPLIN expression as described herein, is likely to not progress and thus remains staged as T1/T2N0 and/or stage I/II. The non-aggressive HNSCC, breast cancer, colorectal cancer or bladder cancer may therefore be treated with monotherapy i.e. surgery only with sufficient surgical margins.

In an aspect of the invention, depending on the HNSCC, breast cancer, colorectal cancer or bladder cancer and embodiment in question, non-aggressive HNSCC, breast cancer, colorectal cancer or bladder cancer may refer to, for example less than 60%, less than 50%, less than 40%, less than 30%, less than 20% or less than 10% a likelihood of the HNSCC, breast cancer, colorectal cancer or bladder cancer progressing beyond T1/T2N0 and/or stage I/II within 1 year, 2 years, 3 years, 4 years or 5 years after the primary diagnosis.

In an aspect of the invention, as a further non-limiting example, non-aggressive HNSCC, breast cancer, colorectal cancer or bladder cancer may refer to a probable favourable course of the disease over time. "Prolonged overall survival", "prolonged disease-free survival", "prolonged recurrence-free survival" and "prolonged progression-free survival", when compared to the median outcome of HNSCC, breast cancer, colorectal cancer or bladder cancer for example, are non-limiting examples of non-aggressively behaving HNSCC, breast cancer, colorectal cancer or bladder cancer. Depending on the embodiment in question, non-aggressive HNSCC, breast cancer, colorectal cancer or bladder cancer may refer to, for example at least 20%, at least 30%, at least 40%, at least 50%, at least 60%, at least 70%, at least 80% or at least 90% chance of surviving more than 1 year, more than 2 years, more than 3 years, more than 4 years or more than 5 years after primary diagnosis of HNSCC, breast cancer, colorectal cancer or bladder cancer.

In an aspect of the invention, in summary, increased expression level of EPLIN may be an indicator of aggressive HNSCC, breast cancer, colorectal cancer or bladder cancer, such as HNSCC, breast cancer, colorectal cancer or bladder cancer showing invasiveness and/or reduced overall survival; whereas non-increased or decreased expression level of EPLIN may be an indicator of non-aggressive HNSCC, breast cancer, colorectal cancer or bladder cancer, such as HNSCC, breast cancer, colorectal cancer or bladder cancer showing no invasiveness and/or prolonged overall survival.

Analyses described herein revealed statistically significant associations between EPLIN expression level and clinical outcomes, such that patients with lower EPLIN burden survived longer and thus had less aggressive disease. For example, as described in the experimental part, HNSCC patients with increased EPLIN expression had significantly shorter overall survival (p=0.009 or p=0.011) than HNSCC patients with non-increased or decreased EPLIN expression. Increased EPLIN expression was found to be a marker for aggressive cancer and an adverse prognostic marker in a cancer such as HNSCC, breast cancer, colorectal cancer or bladder cancer.

The analyses described herein combined clinical data of HNSCC patients including life expectancy, cancer overall survival (OS), given cancer treatments, disease-specific survival (DSS), tumor TNM classification, tumor staging classification, tumor residive information, tumor locoregional information and tumor International Classification of Diseases (ICD) classification with protein expression assays. As illustrated in FIGS. 1C and 1D, increased EPLIN expression was found to prognose reduced overall HNSCC survival. Thus, non-increased or decreased EPLIN expression indicated non-aggressive cancer and/or a good prognosis, whereas increased EPLIN expression indicated aggressive cancer and/or a poor prognosis.

Tumors that are small-size (T1/T2 or stage I/II) and lymph node metastasis negative (N0) at the date of diagnosis are conventionally assumed to be non-aggressive. These small-size tumors are mainly treated by surgery i.e. removal of primary tumor because of the local nature of the disease and small size of the tumor. In the analyses described herein, in a tissue database originating from HNSCC patients diagnosed and treated in southwest Finland area during 2005-2010, 232 patients met the clinical criteria and were thus diagnosed with T1/T2N0 or stage I/II disease. Even though these patients were supposed to have non-aggressive disease and therefore good prognosis, 44% (102 out of 232 patients) died during the 5-year follow-up time. The highest mortality rate, 55 patients, was recorded within two years after primary diagnosis. The T1/T2N0 or stage I/II patient groups are challenging to treat for cancer, because there has not been a biomarker available for identifying the patients with aggressive tumors even though due to its small size and/or early stage the tumor does not give indication of aggressiveness.

Figure 4:
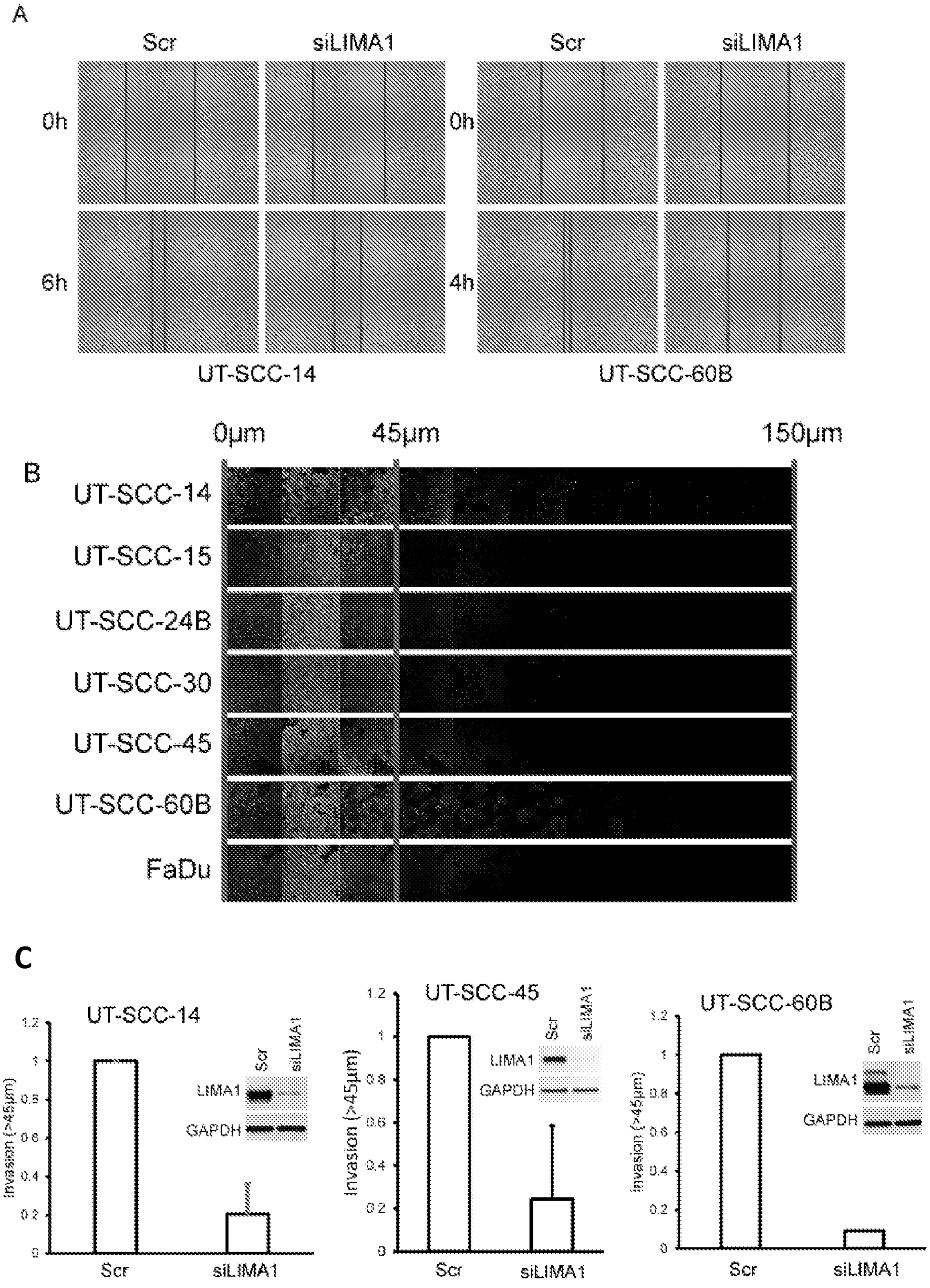
FIG. 4 illustrates the results of siRNA silencing of EPLIN.
Figure 5:
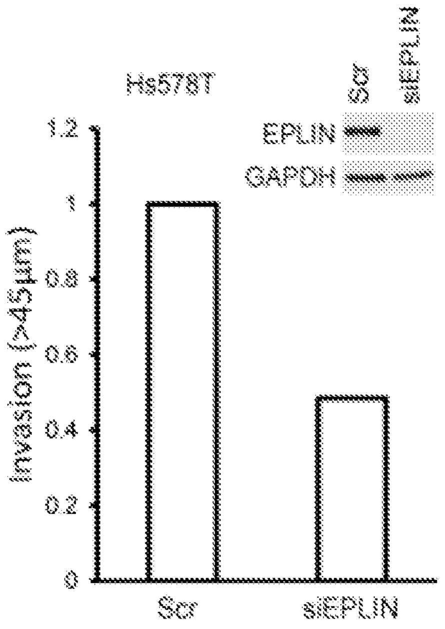
FIG. 5 shows depletion of LIMA1 attenuated cell invasion in breast cancer (BC) cells (Hs578T).

Importantly, it was found in the analyses described herein that an increased EPLIN expression indicates aggressive cancer, whereas non-increased or decreased EPLIN expression indicates non-aggressive cancer among patients having small-size T1/T2N0 or stage I/II tumors at the time of diagnosis (FIGS. 1C and 1D). EPLIN expression also differentiates between aggressive and non-aggressive cancer (FIGS. 3A-C) and is associated with cancer invasiveness (FIGS. 4 and 5). In an aspect of the invention, EPLIN thus is a diagnostic marker for aggressiveness of cancer such as HNSCC, breast cancer, colorectal cancer or bladder cancer.

On the other hand, an increased EPLIN expression prognosticates reduced overall cancer survival among HNSCC patients having small-size T1/T2N0 or stage I/II stage tumors at the time of diagnosis (FIGS. 1C and 1D). Thus, in one aspect of the invention, non-increased or decreased EPLIN expression indicates a good prognosis in small-size T1/T2N0 and/or stage I/II cancers, whereas an increased expression indicates a poor prognosis.

As discussed hereinabove, increased expression of EPLIN has previously been associated with non-aggressive, possibly benign behaviour of the tumor. Contrary to this, it was found in the analyses described herein that aggressive cancer is associated with increased EPLIN expression. Immunohistochemical staining showed EPLIN expression to be essentially located in the invasive front of the tumor in HNSCC patient samples (FIG. 1A). This finding and others reported herein indicate EPLIN is a biomarker particularly for aggressive cancers showing invasive behaviour. In addition, the results of the analyses described herein on cancer cell lines and cancer tumor samples indicate a connection between increased expression of EPLIN and poor prognosis.

Moreover, the findings described herein indicate that EPLIN protein assay can provide diagnosis of aggressive cancer (Table 1, FIGS. 1E and 3A-C). In the prospective analysis presented herein, all patients with evidence of lymph node metastatic HNSCC disease (N1/N2 according to TNM staging), displayed increased EPLIN expression in their primary tumors. The most aggressive disease i.e. worst outcome was in those patients whose normal tissue from an area adjacent to the tumor also showed EPLIN protein expression. These results from the prospective study indicate that detection of EPLIN expression in already small-size tumors (T1/T2N0) provides an estimate of aggressiveness of the tumor.

Accordingly, determining EPLIN expression may be useful in identifying patients with poor prognosis, with aggressive disease and in need of extended surgical and/or oncological treatment. For example, determining EPLIN expression can be useful in stratifying patients and selecting and assigning therapy to patients, e.g. by identifying patients with non-increased or decreased EPLIN expression for whom curative treatment might be sufficient by monotherapy with surgery and patients with increased EPLIN expression for whom treatment should be extended.

For example, extended treatment of cancer may comprise monotherapy by dissection or radiotherapy in combination with chemotherapy and/or dissection. Extended treatment of HNSCC may comprise monotherapy by neck dissection or radiotherapy in combination with chemotherapy and/or neck dissection. "Lymph node dissection" or "dissection" as used herein refers to the removal of regional lymph nodes, and for example in the case of HNSCC, removal of cervical lymph nodes by neck dissection. Extended treatment in cancers thus may refer to removal of regional lymph nodes by dissection or radiotherapy in combination with chemotherapy and/or dissection, whereas "treatment by surgery" or "surgery" may refer to removal of the primary tumor only leaving lymph nodes intact. Expression analysis may be performed by any suitable method such as Western blotting or immunohistochemical staining of EPLIN as described in the analyses herein.

The findings presented herein further demonstrate that determining EPLIN expression facilitates personalized referral to treatment with epidermal growth factor receptor (EGFR) inhibitors (EGFRi). EGFR is known to have a significant role in regulation of cancer invasiveness and aggressiveness, and target therapy drugs have been developed against EGFR. EGFRi drugs are new generation cancer drugs which have a direct effect on EGFR function. However, it has remained a challenge to identify patients to whom administering EGFRi drugs provides efficient treatment. A mass spectrometry analysis presented herein indicates strong interaction between EPLIN and EGFR (FIG. 6A). Also, silencing EPLIN expression reduces activity of EGFR in breast cancer cells (FIG. 6B) and decreases sensitivity of HNSCC cells to EGFRi drugs EGFR tyrosine kinase inhibitors Erlotinib, AZD9291, Afatinib, Cetuximab, AZD8931, Gefitinib and Neratinib, with Erlotinib having the most prominent effect (FIG. 6C). A high EPLIN expression was shown to correlate with an increased EGFRi sensitivity. EGFRi drugs Erlotinib, Gefitinib, Canertinib and Afatinib were shown in our study to have the highest sensitivity, and thus they represent target therapy drugs in EPLIN positive HNSCC cancer cell lines. Particularly, Erlotinib and Afatinib were proven to function as precision therapy in several EPLIN positive HNSCC patients (FIG. 7A).

The findings reported herein indicate that in addition to determining or diagnosing aggressiveness of cancer based on the level EPLIN protein expression, EPLIN can also be used in selecting treatment and/or assigning treatment to a cancer patient based on the level of EPLIN expression because the characteristics causing aggressive behavior of cancer can be undone with medicinal treatment directed to EGFR protein. The findings further show that the method based on determining EPLIN protein expression can identify aggressively progressing tumors directly from patient samples and that the identification can be done at a very early stage while the tumor is still small-size. In addition, we have shown that EPLIN regulates invasiveness of cancer cells and interacts with EGFR which is known to have a significant role in regulating aggressiveness of many cancers. Also, we have shown directly from HNSCC patient samples that expression of EPLIN specifically prognosticates the effectiveness of EGFRi drugs. The inherent expression of EPLIN in the cancer prognosticates the efficacy of EGFRi better than EGFR expression (FIG. 7B). These findings as a whole enforce the potential of EPLIN in cancer diagnostics and in selecting treatment for cancer patients.

Extended treatment of cancer may thus comprise chemotherapy treatment with one or more EGFR inhibitors. Optionally, extended treatment may further comprise dissection and/or radiotherapy. The one or more EGFR inhibitor(s) are preferably selected from Erlotinib, AZD9291, Afatinib, Cetuximab, AZD8931, Gefitinib and Neratinib.

In one aspect, the invention provides an in vitro method of selecting a suitable treatment to a subject diagnosed with cancer, wherein the method comprises or consists of determining the expression level of EPLIN in a sample obtained from the subject, comparing the assayed expression level of EPLIN to a control level, and selecting a treatment on the basis of said comparison. In the method of selecting treatment, a treatment comprising i) dissection as monotherapy or radiotherapy in combination with chemotherapy and/or dissection; or ii) chemotherapy with one or more EGFR inhibitors and optionally dissection and/or radiotherapy;

is selected when expression of EPLIN is increased. Alternatively, a treatment comprising surgery is selected when expression of EPLIN is non-increased or decreased. Preferably, no dissection, no chemotherapy and no radio-therapy are selected when expression of EPLIN is non-increased or decreased. Notably, said selection method does not necessarily involve therapeutic intervention but only provides help in clinical decision-making. In an embodiment, the selection of treatment is a further step to the method of diagnosing aggressiveness or determining prognosis or predicting response to treatment of cancer i.e. the method further comprises a step of selecting treatment to the subject on the basis of the comparison of expression levels. In an embodiment, said control level is the level of EPLIN expression in a sample from an apparently healthy i.e. non-diseased subject.

In another aspect, the invention provides the use of EPLIN as a biomarker for selecting treatment to a subject diagnosed with cancer.

In one aspect, the invention provides an in vitro method of suggesting a suitable treatment to a subject diagnosed with cancer, wherein the method comprises or consists of determining the expression level of EPLIN in a sample obtained from the subject, comparing the assayed expression level of EPLIN to a control level, and suggesting a treatment on the basis of said comparison. In the method of suggesting treatment, a treatment comprising i) dissection as monotherapy or radiotherapy in combination with chemotherapy and/or dissection; or ii) chemotherapy with one or more EGFR inhibitors and optionally dissection and/or radiotherapy;

is suggested when expression of EPLIN is increased. Alternatively, a treatment comprising surgery is suggested when expression of EPLIN is non-increased or decreased. Preferably, no dissection, no chemotherapy and no radiotherapy are selected when expression of EPLIN is non-increased or decreased. Notably, said suggestion method does not necessarily involve therapeutic intervention but only provides help in clinical decision-making. In an embodiment, the suggesting of treatment is a further step to the method of diagnosing aggressiveness or determining prognosis or predicting response to treatment of cancer i.e. the method further comprises a step of suggesting treatment to the subject on the basis of the comparison of expression levels. In an embodiment, said control level is the level of EPLIN expression in a sample from an apparently healthy i.e. non-diseased subject.

In another aspect, the invention provides the use of EPLIN as a biomarker for suggesting treatment to a subject diagnosed with cancer.

In a further aspect, the invention provides an in vitro method of assigning a treatment to a subject diagnosed with cancer, wherein the method comprises or consists of determining the expression level of EPLIN in a sample obtained from the subject, comparing the assayed expression level of EPLIN to a control level, and assigning a treatment on the basis of said comparison. In the method of assigning treatment, a treatment comprising i) dissection as monotherapy or radiotherapy in combination with chemotherapy and/or dissection; or ii) chemotherapy with one or more EGFR inhibitors and optionally dissection and/or radiotherapy;

is assigned when expression of EPLIN is increased. A treatment comprising surgery is assigned when expression of EPLIN is non-increased or decreased. Preferably, no dissection, no chemotherapy and no radiotherapy are selected when expression of EPLIN is non-increased or decreased. In an embodiment, said control level is the level of EPLIN expression in a sample from an apparently healthy i.e. non-diseased subject.

In yet another aspect, the invention provides the use of EPLIN as a biomarker for assigning treatment to a subject diagnosed with cancer.

In a further aspect, the invention provides an in vitro method of predicting response to treatment of cancer in a subject, wherein the method comprises or consists of determining the expression level of EPLIN in a sample obtained from the subject, comparing the assayed expression level of EPLIN to a control level, and predicting response to treatment on the basis of said comparison. In the method of predicting response to treatment, the treatment comprises i) surgery or dissection or radiotherapy in combination with chemotherapy and/or dissection; or ii) surgery or chemotherapy with one or more EGFR inhibitors and optionally dissection and/or radiotherapy.

The treatment may already have been given to the subject or is planned to be given to the subject. In the method of predicting response, increased expression of EPLIN is indicative of negative response to treatment, whereas non-increased or decreased expression of EPLIN is indicative of positive response to treatment. In an embodiment, the control level is the level of EPLIN expression in a normal control i.e. a sample from an apparently healthy i.e. non-diseased subject. In another embodiment, the control level is determined from a sample collected from said subject treated for cancer before the treatment.

In a yet further aspect, the invention provides the use of EPLIN as biomarker for predicting response to treatment of cancer in a subject.

The analyses described herein also characterized the roles of EPLIN alpha and EPLIN beta isoforms in cancer biology. As illustrated in FIG. 1E, it was found that both EPLIN isoforms alpha and beta were detected in HNSCC cell lines (UT-SCC) maintained as cell cultures. However, all EPLIN positive fresh HNSCC patient tumor samples contained high EPLIN alpha expression, whereas very low, barely detectable EPLIN beta expression could be seen in Western blot analyses in very few HNSCC cancer samples. Cancer such as HNSCC therefore was found to associate particularly with EPLIN alpha isoform.

Of the two EPLIN isoforms, the EPLIN alpha isoform is particularly related to aggressive tumors and is associated with a poor prognosis. This is evidenced by the analyses described herein, where those HNSCC tumors that express EPLIN alpha were found to show metastasis to local lymph nodes (N1/N2 in TNM staging) (FIG. 1E). Patients showing EPLIN alpha expression thus appear to have an increased risk of developing lymph node metastatic disease, which is the strongest known clinical parameter causing adverse prognosis of cancer for patients such as HNSCC patients.

Moreover, silencing of EPLIN alpha gene expression by the siRNA (small interfering RNA) method was found in the analyses described herein to decrease very effectively the invasive behaviour of cancer cell lines (FIG. 2), whereas silencing of EPLIN beta had a less pronounced effect. Clearly, EPLIN alpha expression has a role in regulating cancer aggressiveness and enhancing the aggressive invasive/metastatic behaviour of cancer which may be associated with a poor prognosis. Determining expression level of EPLIN alpha may also be useful in patient stratification and assigning therapy.

In an aspect of the invention, EPLIN is total EPLIN, EPLIN alpha or EPLIN beta for any purpose set forth herein. As used herein, the term "total EPLIN" refers to both isoforms alpha and beta of EPLIN. The terms "total EPLIN" and "EPLIN" may be used interchangeably.

In other words, in the methods and uses and kits of the invention, expression level of total EPLIN, EPLIN alpha or EPLIN beta or any combination thereof may be assayed. Alternatively, expression level of total EPLIN or EPLIN alpha or EPLIN beta may be assayed. Alternatively, the expression level of total EPLIN and EPLIN alpha and/or EPLIN beta is assayed. Alternatively, expression level of total EPLIN, and EPLIN alpha or EPLIN beta is assayed to determine a ratio between total EPLIN and EPLIN alpha or EPLIN beta. The level of EPLIN alpha and/or EPLIN beta may be compared to the other EPLIN isoform or total EPLIN to determine a ratio of one or both isoforms to total EPLIN or to each other. An increased level or ratio of EPLIN alpha as compared to total EPLIN or EPLIN beta and optionally further compared to a control level or corresponding ratio determined from a control may indicate aggressive cancer or poor prognosis or negative response to treatment.

In some other implementations, the present method of determining the probable outcome of cancer may further include therapeutic intervention. Once an individual is identified to have a certain probable outcome of the disease, he/she may be subjected to an appropriate therapeutic intervention, such as a therapy selected from radiotherapy, immunotherapy, chemotherapy, surgery and dissection or any combination thereof. Thus, in some embodiments, the present invention provides a method of treating cancer, in a subject in need thereof, wherein a biological sample obtained from the subject is contacted with a reagent that specifically detects EPLIN, and determining whether or not the expression of EPLIN is increased, non-increased or decreased in said sample by comparing said expression with a control. If said expression is increased, the subject should be assigned to or treated with a treatment regime comprising i) dissection as monotherapy or radiotherapy in combination with chemotherapy and/or dissection; or ii) chemotherapy with one or more EGFR inhibitors and optionally dissection and/or radiotherapy, whereas if said expression is non-increased or decreased, the subject should be assigned to or treated with a treatment regime comprising surgery and preferably no dissection, no chemotherapy and no radiotherapy. To put it differently, the method comprises administering i) dissection as monotherapy or radiotherapy in combination with chemotherapy and/or dissection; or ii) chemotherapy with one or more EGFR inhibitors and optionally dissection and/or radiotherapy to subjects with increased EPLIN expression as compared to a control, while administering surgery and preferably no dissection, no chemotherapy and no radiotherapy to subjects with non-increased (i.e. normal) or decreased EPLIN expression.

In some embodiments, the prognosis of cancer on the basis of EPLIN expression is not finally determined. In such embodiments, the method is not by itself determinative of the prognosis of cancer but can indicate that further prognostic testing is needed or would be beneficial. Therefore, EPLIN may be used in combination with one or more other prognostic methods or markers for the final determination of the prognosis. As readily understood by those skilled in the art, this applies to other aspects of the invention as well, such as diagnosing or selecting or assigning treatment or predicting response to a treatment.

In some embodiments, the methods of the invention may be based on analysing one or more serial samples obtained from the subject, for example, to detect any changes in the prognosis, and may involve a prediction of a response to a particular treatment or combination of treatments for cancer. In such instances, the prognostication method comprises analysing and comparing at least two samples obtained from the same subject at various time points. The number and interval of the serial samples may vary as desired. The difference between the obtained assessment results serves as an indicator of the course of the cancer and risk of relapse. EPLIN may thus be used for various monitoring purposes such as monitoring for cancer progression over time, monitoring for or determining any possible cancer remission, monitoring for or determining any possible recurrence or relapse, monitoring for or determining the presence of minimal residual disease, e.g. during the first remission phase after therapy and monitoring for or determining response to treatment. Further uses of EPLIN include, but are not limited to, patient grouping or stratification.

As readily understood by those skilled in the art, also the other uses of EPLIN mentioned above may be formulated as methods for the indicated purposes.

In the methods disclosed above, the step of assaying the level of EPLIN expression in one or more samples obtained from the subject may be carried out by contacting the sample with a reagent specific for EPLIN and thus suitable for determining the expression level of EPLIN. Non-limiting examples of suitable reagents and techniques for determining EPLIN expression are disclosed below.

At least two samples obtained from the same subject at various time points may thus be determined to compare the expression level in an earlier sample to the expression level in a sample obtained at a later time point. In this context, the term "increased" expression means that the expression level in the later sample is higher than in the earlier sample. Conversely, the term "decreased" expression in this context means that the expression level in the later sample is lower than in the earlier sample.

The present invention provides advantages not only for individual patient care but also for better selection and stratification of patients for clinical trials. For example, cancer patients grouped on the basis of their EPLIN expression levels could be employed in clinical studies with the aim of developing efficient new personalized therapeutic tools such as new medical procedures or drugs.

Determining the expression level of EPLIN in a sample obtained from a subject whose cancer is to be prognosed or who is to be monitored e.g. for cancer progression, cancer remission, recurrence, relapse, response to treatment, or who is to be subjected to therapy selection or grouped or stratified for any relevant cancer-related purpose, can be determined by any available or future means suitable for this purpose. Said determination may be executed at different molecular levels, preferably at mRNA, cDNA, or protein level as is well known in the art. The present invention is not limited to any determination technique. Thus, in different embodiments, different means or combinations thereof for analysing a biological or clinical sample for the expression of EPLIN may be used.

Generally, determining the level of EPLIN expression at protein level comprises contacting a sample obtained from a subject in need of said determination with a binding body, such as an antibody, specifically recognizing EPLIN polypiptide under conditions wherein the binding body specifically interacts with EPLIN; and detecting said interaction (if any); wherein the presence or degree of said interaction correlates with the presence of EPLIN or the level of EPLIN expression in said sample. Binding bodies alternative to antibodies and fragments thereof suitable for determining EPLIN expression at protein level include but are not limited to oligonucleotide or peptide aptamers, receptors and biologically interacting proteins.

Accordingly, in some embodiments the present invention, expression level of EPLIN may be determined by an immunoassay, which comprises for example the following steps: providing an antibody that specifically binds to EPLIN; contacting a patient sample, preferably comprising permeabilized or disrupted cells, with anti-EPLIN antibody; and detecting the presence of a complex of the antibody bound to EPLIN (if any) in the sample. If desired, the antibody can be fixed to a solid support to facilitate washing and subsequent detection of the complex, prior to contacting the antibody with the sample. After incubating the sample with an anti-EPLIN antibody, the mixture may be washed and the antibody-EPLIN complex formed can be detected. This can be accomplished by e.g. using a detectable antibody, i.e., detectably labeled antibody, or an antibody labelled with an enzyme and incubating the complex with a detection reagent, i.e. substrate of the enzyme. Alternatively, EPLIN can be detected using an indirect assay, wherein, for example, a second, labeled antibody is used to detect the antibody-EPLIN complex formed.

In some embodiments, the expression level of EPLIN may be determined using a non-competitive assay format. Non-competitive immunoassays, also known as reagent excess assays, sandwich assays, immunometric assays or two-site assays, generally involve use of two antibodies targeting different epitopes in the antigen, one antibody for antigen capture and the other labeled for detection. A person skilled in the art will be well capable of establishing a binding assay for measuring the level of EPLIN alone or in relation with any control. Accordingly, formation of the antibody-EPLIN complex may be determined using any of a number of well-recognized non-competitive immunological binding assays. Useful assays include, for example, enzyme immune assays (EIA) such as enzyme-linked immunosorbent assay (ELISA); fluorescent immunosorbent assays (FIA) such as time-resolved immunofluorometric assays (TR-IFMA); chemiluminescence immunoassays (CLIA) and radioimmune assays (RIA).

Depending on the assay type employed, either the first antibody or the second antibody, or both, may be conjugated or otherwise associated with a detectable label selected from the group including, but not limited to, optical agents such as fluorescent labels including a variety of organic and/or inorganic small molecules and a variety of fluorescent proteins and derivatives thereof, phosphorescent labels, chemiluminescent labels, and chromogenic labels; radioactive labels such as radionuclides that emit gamma rays, positrons, beta or alpha particles, or X-rays, and enzymes such as alkaline phosphatase (AP) and (horseradish) hydrogen peroxidase (HRP). Said association can be direct, e.g. through a covalent bond, or indirect, e.g. via a secondary binding agent, a chelator, or a linker. Techniques for conjugating or otherwise associating detectable agents to antibodies are well known and antibody labelling kits are commercially avail-able from dozens of sources. One or both of the antibodies may also be expressed as fusion proteins with a detectable label or a detection tag by recombinant techniques.

In some embodiments of non-competitive immunoassays, the detection antibody is detectably labelled. In some other embodiments, the detection antibody is recognized by a further antibody comprising a detectable label. In some still other embodiments, the detection antibody comprises a tag that is recognizable by a further antibody comprising a detectable label. In some still further embodiments, the detection antibody and said further antibodies are labelled with the same label, e.g. for improving sensitivity. In some other embodiments, the detection antibody and said further antibodies are labeled with different labels.

Immunoassays suitable for carrying out the method of the present invention include solid-phase immunoassays, such as lateral flow assays and conventional sandwich assays carried out on a solid surface such as glass, plastic, ceramic, metal or a fibrous or porous material such as paper, in the form of e.g. a microtiter plate, a stick, a card, an array, a sensor, a bead, or a microbead. Said solid-phase immunoassay may be either heterogeneous or homogeneous. In heterogeneous assays, any free antigens or antibodies are physically separated from immunocomplexes formed, e.g. by washings, while no such separation is necessary in homogeneous assays including the many forms of biosensors.

Suitable homogeneous immunoassays are not limited to solid-phase assay formats but encompass also homogeneous immunoassays carried out in solution. Such in-solution immunoassays are particularly advantageous because neither immobilization nor washing steps are required, making them simple and easy to perform. Thus, in some embodiments, the immunoassay is liquid-based homogeneous immunoassay.

Further examples of suitable methods for determining the expression level of EPLIN at protein level include conventional Western blot assays, dot blot assays and assay formats based on immunohistochemistry. Moreover, for example flow cytometry, such as fluorescence-activated cell sorting (FACS), may be used for detecting antibody-EPLIN complexes. Moreover, techniques suitable for determining the expression level of EPLIN at protein level include MS-based detection methods, such as selected reaction monitoring (SRM), SWATH and mass cytometry from cancer cell samples based on the unique peptide. Also, in such embodiments, the method may include comparing the expression level of EPLIN with that of a control biomarker.

Applicable methods for use in determining EPLIN expression at nucleic acid level include but are not limited to microarrays, which are a collection of nucleic acid, e.g. DNA, spots attached to a solid surface. Each DNA spot contains an oligonucleotide of a specific DNA sequence, known as a probe or capture probe. These can consist of a short section of a gene or other oligonucleotide such as DNA or LNA element that are used to hybridize target cDNA, mRNA or cRNA (also called anti-sense RNA) in a sample under high-stringency conditions. Probe-target hybridization can be detected and/or quantified e.g. by detection of fluorophore-, silver-, or chemiluminescence-labeled target nucleic acids to determine their relative abundance in the sample. In some array types a recognition element (transducer) capable of converting a surface-bound probe-target nucleic acid interaction into a quantifiable signal may be incorporated. Among the several different types of transducers available, especially those based on electrochemical or optical detection are popular in the art. Similarly to other nucleic acid analysis methods, both types of sensors can either be run as label-free or label-using and also divided to heterogeneous and homogeneous assay formats based on the requirement for washing.

One suitable application is the NanoString™'s nCounter® technology, which is a variation on the DNA microarray. It uses molecular "barcodes" and microscopic imaging to detect and count up to several hundred unique transcripts in one hybridization reaction. Each color-coded barcode is attached to a single target-specific probe corresponding to a gene of interest. In some embodiments the use of an array-based technology such as the NanoString™ is beneficial in order to detect EPLIN expression.

In accordance with the above, the expression of EPLIN at nucleic acid level may be determined using any suitable method with or without nucleic acid amplification. For example, EPLIN mRNA may be first converted into its complementary cDNA with the aid of a reverse transcriptase, followed by DNA amplification, e.g. by reverse transcriptase PCR (RT-PCR) including but not limited to quantitative PCR (qPCR), also known as real-time PCR. The presence, absence or concentration of the expressed EPLIN mRNA polynucleotide or an amplification product thereof may be assessed according to methods available in the art, for example by using an EPLIN-specific capture or detection probe. Further potential methods suitable for determining the expression of EPLIN at nucleic acid level, with or without a reverse transcription step and/or a nucleic acid amplification step depending on the method selected, include but are not limited to RNase protection assays, molecular beacon-based oligonucleotide hybridization assays, melting curve analysis combined with oligonucleotide probes and/or intercalating labels, gel electrophoresis analysis, Southern blotting, microarrays such as DNA microarrays and RNA microarrays, direct probing, and signal accumulation assays.

The detection of hybridization complexes can be carried out by any suitable method available in the art. Hybridization complexes may in some assay methods be physically separated from unhybridized nucleic acids (e.g. by employing one or more wash steps to wash away excess target mRNA/cDNA, the probe, or both), and detectable labels bound to the complexes are then detected. More often, however, homogeneous detection is employed where no physical separation of hybridized and unhybridized molecules is required. In nucleic acid amplification assays, homogeneous detection may be performed as a separate step after amplification, i.e. using homogeneous end-point detection. The accumulation of the amplicon can also be homogeneously monitored during the amplification assay by use of qPCR type of methods. The various homogeneous detection methods can further be classified into probe-using and non-probe-using formats.

Detectable labels refer to radioactive, fluorescent, biological or enzymatic tags or labels of standard use in the art. A detectable label can be conjugated to either the oligonucleotide probe or the target polynucleotide. As is evident to those skilled in the art, the choice of a particular detectable label dictates the manner in which it is bound to the probe or the target sequence, as well as the technique to be used for detection. Although the present invention is not specifically dependent on the use of a label for the detection of a particular nucleic acid sequence, such a label might be beneficial, by increasing the sensitivity or specificity of the detection and simplifying the multiplexing of the assays. Furthermore, a detectable label may better enable automation.

Intercalating dyes (e.g. SYBR® Green) can be used to detect the amplification of the DNA fragment of interest during a nucleic acid amplification reaction such as PCR. Intercalation occurs when ligands of an appropriate size and chemical nature position between the planar base pairs of DNA. These ligands are mostly polycyclic, aromatic, and planar, and therefore often make suitable nucleic acid stains. The intensity of fluorescence increases respectively during the amplification and it can be measured in real-time without the need of separate oligonucleotide probes.

As appreciated by those skilled in the art, a variety of controls and additives may be employed to improve accuracy of hybridization assays. For instance, samples may be hybridized to an irrelevant probe and/or treated with RNAse A prior to hybridization, to assess false hybridization or prevent unspecific or unwanted effects.

In some embodiments, determining the expression of EPLIN is performed by sequencing techniques. Numerous methods suitable for this purpose have been described in the art and include, but are not limited to, traditional Sanger sequencing and next-generation sequencing (NGS) techniques. The present embodiments are not limited to any branded technique.

A representative commercial platform suitable for use in accordance with some embodiments of the invention, wherein the presence or quantity of EPLIN, if any, is detected by sequencing, is Illumina®'s sequencing by synthesis (SBS) technology, particularly TruSeq® technology. Applying TruSeq® technology requires that two oligonucleotide probes, which hybridize upstream and downstream of the region of interest, are designed and synthetized. Each probe contains a unique, target specific sequence and a universal adapter sequence. An extension-ligation reaction is used to unite the two probes and create a library of new template molecules with common ends. Adapter-ligated DNA is then subjected to PCR amplification, which adds indexes and sequencing primers to both ends. Sequencing may then be performed by any suitable equipment, such as MiSeq® sequencer, utilizing a reversible terminator-based method enabling detection of single bases as they are incorporated into growing DNA strands.

Non-limiting examples of suitable equipment for the present sequencing purposes include Illumina® Sequencers, such as MiSeq™, NExtSeq500™, and HiSeq™ (e.g. HiSeq™2000 and HiSeq™3000), and Life Technologies'® Sequencers, such as Ion Torrent™ Sequencer and Ion Proton™ Sequencer. It should be understood that utilizing any of these equipments requires that appropriate sequencing technique and chemistry be used.

In some embodiments relating to NGS techniques, detection of EPLIN mRNA is possible with deep sequencing such as a one performed with Illumina® HiSeq™3000 platform, 150 bp reading length and paired-end library.

Further methods suitable for detecting the expression level of EPLIN include, but are not limited to, RNA in situ hybridization technologies such as RNAscope® (Advanced Cell Diagnostics, ACD) and ViewRNA™ (Invitrogen™).

In a further aspect, the present invention provides a kit and use thereof for detecting the expression level of EPLIN in a biological or clinical sample, for any purpose set forth above. Preferably, the kit comprises an EPLIN-specific binding body, such as an anti-EPLIN antibody or at least one EPLIN-specific oligonucleotide, such a probe and/or a primer pair. In some embodiments, the binding body may comprise a detectable label. A person skilled in the art can easily determine any further reagents to be included in the kit depending on the desired technique for carrying out determination of the expression level of EPLIN. Thus, the kit may further comprise at least one reagent for performing for example an immunoassay such as ELISA, a Western blot, immunohistochemical assay, nucleic acid amplification assay, signal amplification assay, in situ RNA hybridization assay, mass spectrometric assay or sequencing assay.

In some embodiments, an appropriate control reagent or sample or a threshold value may be comprised in the kit. The kit may also comprise a computer readable medium, comprising computer-executable instructions for performing any of the methods of the present disclosure.

Experimental Part

LIMA-1/EPLIN Expression in HNSCC

LIMA-1/EPLIN expression analyses were performed as a retrospective analysis on HNSCC patient samples from a clinically validated HNSCC tissue microarray (TMA). The TMA entails clinical data and tumor specimens diagnosed and treated in HNSCC patients in southwest Finland (an area covering one sixth of the total population of Finland) during 2005-2010. The clinical data covers life expectancy, cancer overall survival (OS), given cancer treatments, disease-specific survival (DSS), tumor TNM classification, tumor staging classification, tumor residive information, tumor locoregional information and tumor International Classification of Diseases (ICD) classification. In the TMA, 232 patients met the clinical criteria of small-size tumor and local disease, and were diagnosed with T1/T2N0 disease. Even though these patients were supposed to have non-aggressive disease and relatively good prognosis, 44% (102 out of 232 patients) died during 5-year follow-up time. The highest mortality rate, 55 patients, was recorded within two years after diagnosis.

Figure 1B:
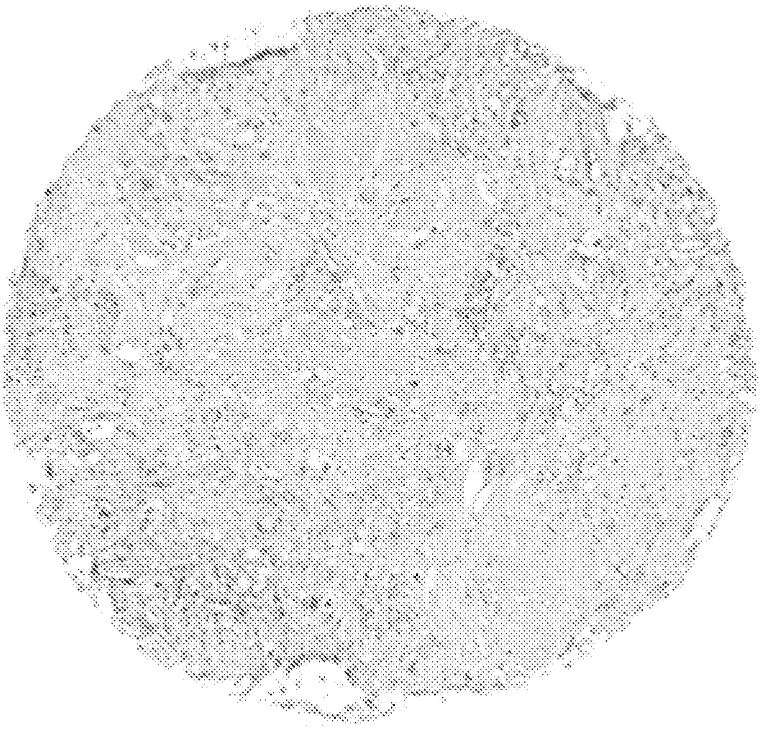
Figure 1C:
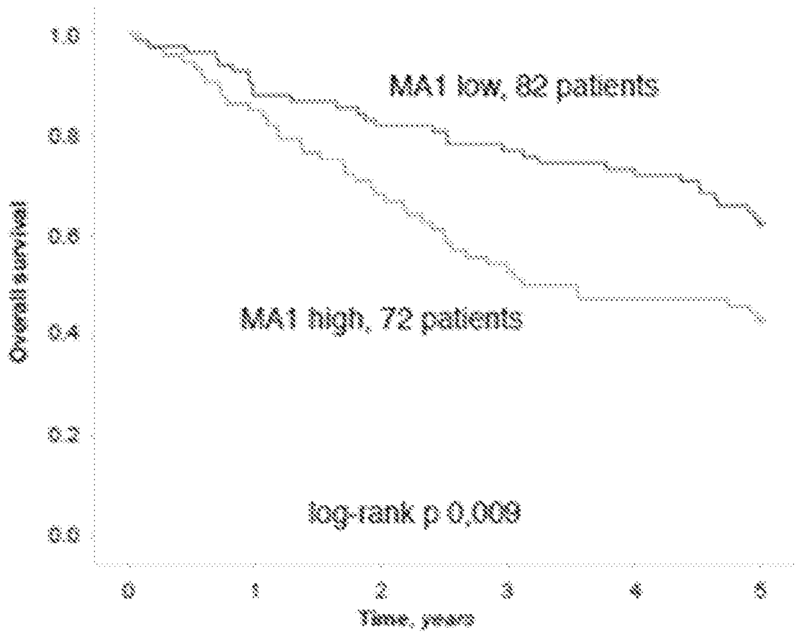
Figure 1D:
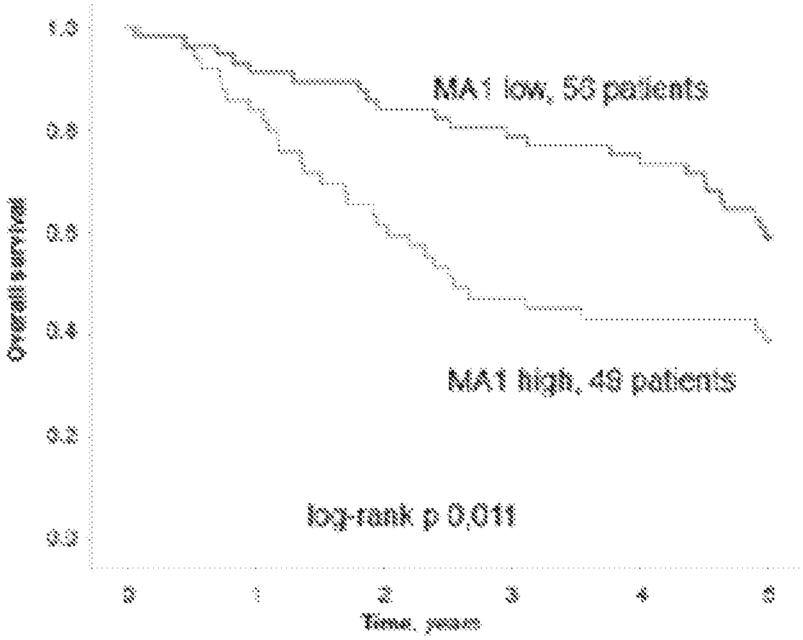
Figure 1E:
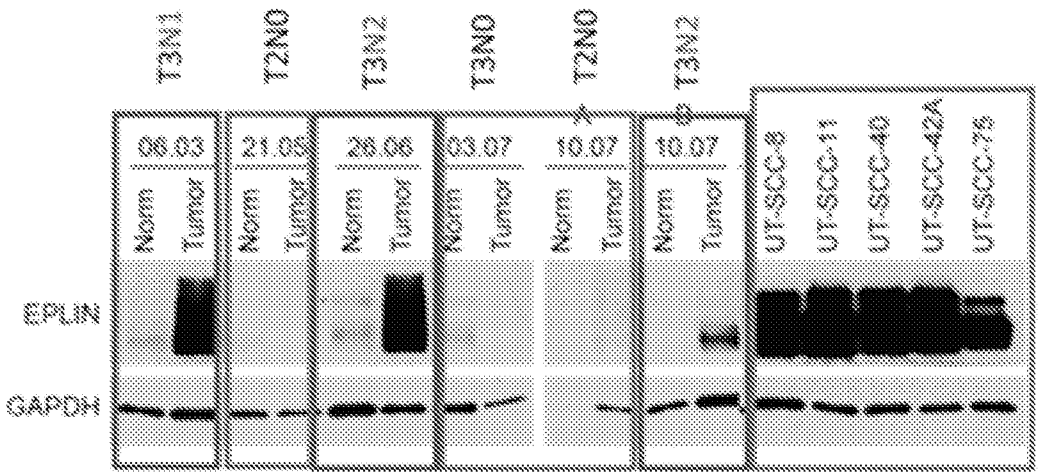

Illustrated in FIGS. 1A and 1B are immunohistochemical stains of exemplary HNSCC tumor samples from the TMA with an antibody specific for EPLIN. FIG. 1A exhibits increased EPLIN expression in an HNSCC tumor sample, and FIG. 1B exhibits non-increased EPLIN expression in a HNSCC tumor sample. Increased EPLIN expression is associated with aggressive behaviour of the cancer due to e.g. an increased invasive character, and accordingly, the immunohistochemical staining also demonstrates that EPLIN expression is located in the invasive front of the tumor (FIG. 1A). Non-increased EPLIN expression is associated with non-aggressive cancer showing non-invasive behaviour (FIG. 1B).

EPLIN expression analyses were performed in the retrospective analysis with immunohistochemical staining. Patient samples were categorized into those with high or low EPLIN expression. As used herein, the term "high" means that EPLIN expression is increased as indicated by intense staining as exemplified in FIG. 1A. As used herein, the term "low" means that EPLIN expression is non-increased or decreased as indicated by weak or essentially nonexistent EPLIN staining as exemplified in FIG. 1B.

As illustrated in FIG. 1C, in a total of 154 patients with small-size (T1/T2N0 and less than 2 cm in its greatest dimension at the time of diagnosis) HNSCC tumors a high LIMA-1/EPLIN expression (72 patients, marked in FIG. 1C as MA1 high) is associated with a significantly (log-rank $p=0.009$) worse overall survival as compared to overall survival of HNSCC patients with low LIMA-1/EPLIN expression (82 patients, marked in FIG. 1C as MA1 low). Moreover, as illustrated in FIG. 1D, in a total of 105 patients with small-size (stage I/II) HNSCC tumors a high LIMA-1/EPLIN expression (49 patients, marked in FIG. 1D as MA1 high) is associated with a significantly (log-rank $p=0.011$) worse overall survival as compared to overall survival of HNSCC patients with low LIMA-1/EPLIN expression (56 patients, marked in FIG. 1D as MA1 low). Thus, EPLIN expression analysis can provide diagnosis of aggressive HNSCC as well as provide a prognosis of the HNSCC.

FIG. 1E shows Western blot results for EPLIN protein expression in HNSCC cell lines (UT-SCC; Lepikhova et al. 2018) as well as in normal tissue (Norm) and HNSCC tumor (Tumor) samples collected from HNSCC patients of the retrospective analysis. Tumor size (T) and metastasis to local lymph nodes (N) of HNSCC patients are indicated above the patients' Western blot analyses. Low EPLIN expression is associated with non-metastatic cancers i.e. N0 and also M0 grade.

A prospective analysis was performed by collecting prospective, non-selective HNSCC patient sample material from 15 HNSCC patients during 2019. The patients had given written consent to the study. All patients received curative treatment for HNSCC. Tissue samples were collected during surgery from all 15 patients from the HNSCC tumor as well as from apparently normal and healthy, adjacent tissue next to the tumor, in a so-called healthy tissue area. Expression analysis was performed by Western blot analysis of the tissue samples, where EPLIN alpha and beta isoforms were detected by a primary antibody binding both isoforms. GAPDH was used as a loading control in the Western blot.

Prospective follow-up of the 15 patients indicated (Table 1) that EPLIN expression analysis can provide diagnosis of aggressive HNSCC as well as provide prognosis of the HNSCC according to the following rationale. Of the group of follow-up patients 4 out of 15 were negative for EPLIN expression as determined by Western blotting, and 11 out of 15 were positive for EPLIN expression. As used herein, the term "negative" means that EPLIN expression is non-increased or decreased as seen from essentially no presence of EPLIN in the Western blot. As used herein, the term "positive" means that EPLIN expression is increased as seen from the presence of EPLIN in the Western blot.

In all patients with evidence of lymph node metastatic disease (7 out of 15 patients; N1/N2 according to TNM staging), primary tumors showed increased EPLIN expression. The most aggressive cancer and poorest prognosis was in those patients (3 out of 15 patients) whose "normal tissue" adjacent to the tumor also showed increased EPLIN expression. The results indicate increased EPLIN expression in the normal tissue to be an early sign of disease when the tissue still appears normal and cannot yet be distinguished as being cancerous or could be used as a sign of micrometastases, field of cancerization or invasive escape of cancer cells from primary tumor to its surrounding tissues. In the three patients with EPLIN expression in normal tissue, progression of HNSCC was seen within <4 months of surgery and 1 patient died of disease progression within <5 months of cancer treatment, which turned out not to be curative unlike assumed at the time of diagnosis. These results from our follow-up studies indicate that detection of increased EPLIN expression not only indicates poor prognosis in small-size tumors (T1/T2N0), but also appears to serve as a prognostic marker in other HNSCC tumors as well.

Figure 2:
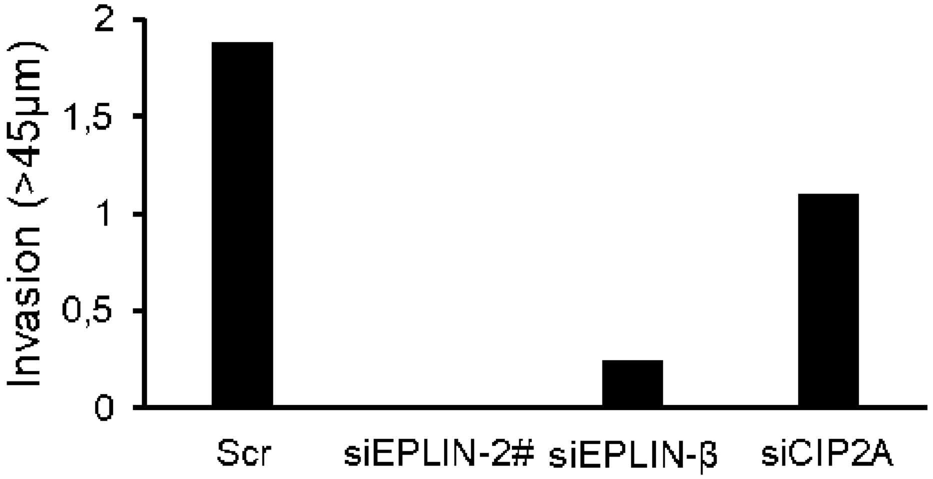
FIG. 2 illustrates the results of an inverted invasion assay after silencing of CIP2A (Cellular Inhibitor of PP2A) and LIMA-1/EPLIN isoforms alpha and beta in a HNSCC cell line (UT-SCC14). Silencing of EPLIN alpha (siEPLIN-2#) caused the most dramatic decrease in inverted invasion compared to EPLIN beta (siEPLIN-β) and CIP2A (siCIP2A).

FIG. 2 illustrates the results of an invert invasion assay after silencing of CIP2A and EPLIN isoforms alpha and beta in the HNSCC cell line UT-SCC14. Cancerous inhibitor of Protein phosphatase 2A (CIP2A) is an inhibitor of the tumor suppressor protein PP2A and is widely present in malignant cells. CIP2A was included in the invert invasion assay as a positive control. Scrambled siRNA (siSCR or SCR) is commonly used in the siRNA silencing method as a negative control and was also used as the negative control in the invert invasion assay. As seen in FIG. 2, silencing of EPLIN alpha (siEPLIN-2#) caused the most dramatic decrease in invert invasion compared to EPLIN beta (siEPLIN-β) and CIP2A (siCIP2A).

Figure 3:
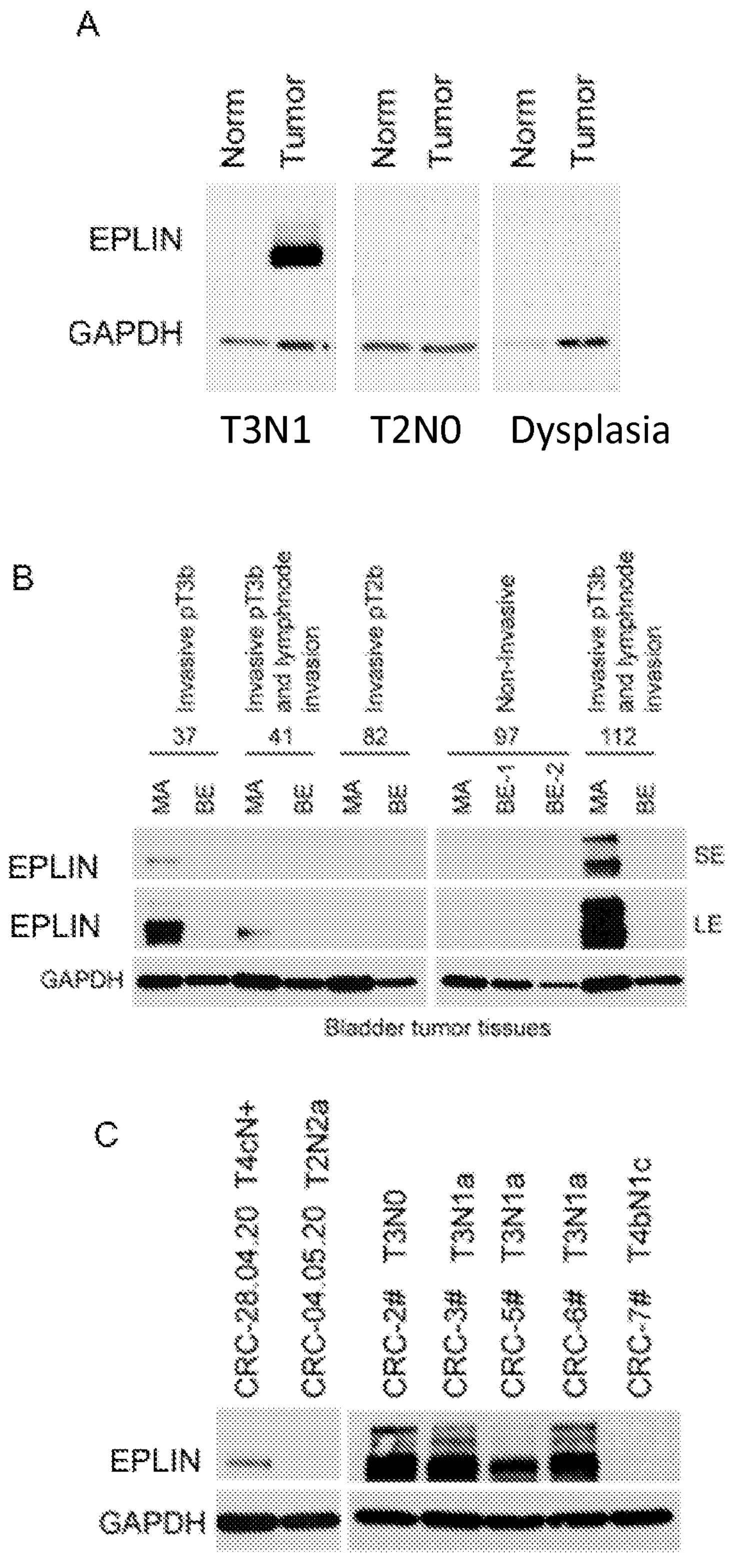
FIG. 3 illustrates Western blot results for EPLIN protein expression in HNSCC (FIG. 3A), bladder cancer (FIG. 3B) and colorectal cancer (FIG. 3C) samples. Aggressive, invasive cancer could be identified based on EPLIN expression.

FIG. 3A illustrates Western blot results for EPLIN protein expression in HNSCC patient tissue samples selected in a blinded manner. GAPDH was used as a loading control in the Western blot. EPLIN acted as a cancer specific biomarker as the samples from the HNSCC patient normal tissue (marked 'Norm' in FIG. 3A) were EPLIN-negative. Additionally, HNSCC patients having aggressive cancer with lymph node metastasis (marked 'T3N1' in FIG. 3A) could be identified with positive EPLIN western blot expression in their tumor. Moreover, HNSCC tumors that were not spread locally or metastasized to lymph nodes (marked 'T2N0' in FIG. 3A) or were classified by a pathologist to dysplasia (marked 'Dysplasia' in FIG. 3A) were all EPLIN negative in western blot analyses. These results show that EPLIN is a cancer-specific biomarker and recognizes the presence of aggressive cancer in a patient-based manner.

LIMA-1/EPLIN Expression in Bladder Cancer and Colorectal Cancer

FIG. 3B illustrates Western blot results for EPLIN protein expression in five bladder cancer patient samples from a nonselected prospective patient group. GAPDH was used as a loading control in the Western blot. By using EPLIN as a biomarker, the normal bladder tissue sample(s) ('BE'=benign) was identified with 100% accuracy from the cancer tissue sample ('MA'=malignant) of the same patient, as all normal tissue samples were EPLIN negative. Additionally, invasive, aggressive bladder cancer tumors with different clinical TNM stagings could be identified via EPLIN protein expression. Three (sample numbers 37, 41 and 112) out of four invasive (locally invasive and/or lymph node invasion) bladder cancer samples were EPLIN positive. Further abbreviations in FIG. 3B are: SE, short exposure in Western blot; LE, long exposure in Western blot.

FIG. 3C illustrates Western blot results for EPLIN protein expression in seven colorectal cancer (CRC) patient samples from a nonselected prospective patient group with different clinical TNM stagings. GAPDH was used as a loading control in the Western blot. Five (CRC-28.04.20, CRC-2#, CRC-3#, CRC-5# and CRC-6#) out of seven invasive CRC samples were found EPLIN positive. Thus, invasive, aggressive CRC tumors could be identified via EPLIN protein expression.

TABLE 1

All patients were M0 in TNM grading at diagnosis.
Nd = not determined; m = month; OK = patient had no sign of disease, treatment had apparently been curative.

| Patient | Tumor at diagnosis | | | Normal tissue | Follow-up | |
|---|---|---|---|---|---|---|
| # | EPLIN | T | N | EPLIN | Months | Status |
| 1 | + | 3 | 1 | − | 11 | New surgery 9m after primary operation, dysplasia |
| 2 | − | 2 | 0 | − | 9 | OK |
| 3 | − | 2 | 0 | − | 9 | OK |
| 4 | + | 3 | 2 | − | 8 | OK |
| 5 | − | 3 | 0 | − | 7 | OK |
| 7 | − | 2 | 0 | Nd | 7 | OK |
| 8 | + | 3 | 0 | − | 7 | Local and distant metastasis 6m after primary operation |
| 12 | + | 2 | 2 | + | 5 | Local metastasis 4m after primary operation |
| 13 | + | 3 | 0 | Nd | 5 | OK |
| 14 | + | 4 | 0 | Nd | 5 | OK |
| 15 | + | 3 | 1 | + | 5 | Exitus, aggressive local recidive |
| 16 | + | 2 | 1 | − | 4 | OK |
| 17 | + | 4 | 0 | Nd | 4 | OK |
| 18 | + | 3 | 2 | − | 4 | OK |
| 19 | + | 2 | 2 | + | 3 | Progressive cancer, poor prognosis |

EPLIN as Regulator of HNSCC and Breast Cancer Migration and Invasion

The effect of silencing EPLIN expression on invasiveness of HNSCC was studied in HNSCC cell lines. FIG. 4 illustrates the results of siRNA silencing of EPLIN ('siLIMA1'). Scrambled siRNA ('Scr') was used in the assay as the negative control with no EPLIN silencing. FIG. 4A illustrates a wound healing assay where cells were seeded appropriately in IncuCyte® ImageLock 96-well plate and cultured for 6-18 hours. The wounds were then made by IncuCyte® WoundMaker. After wounding, the plates were put into Incucyte ZOOM® (Essen Bioscience, UK). The repeated scannings (every 2 h for 48 h) were scheduled in the ZOOM software. Quantification of cell migration was done by Incucyte ZOOM® software. As seen from FIG. 4A, depletion of LIMA1 (=EPLIN) slowed cell migration in UT-SCC-14 and UT-SCC-60B cells.

Inverted invasion assays were performed as described in Jacquemet et al (2016). Briefly, 200 ml of collagen I (concentration 5 mg/ml; PureCol® EZ Gel, Advanced BioMatrix) supplemented with 25 mg/ml FN was used to polymerize in inserts (8 mm ThinCert™; Greiner bio-one®) for 1 h at 37° C. Inserts were then inverted, and cells were seeded directly onto the opposite face of the filter. Transwell inserts were placed in serum-free medium, and medium supplemented with 10% FBS was placed on top of the matrix, providing a chemotactic serum gradient. Where appropriate, compounds were added to both the lower and upper chambers. Migrating cells were fixed 48 h after seeding using 4% PFA for 2 h, permeabilized in 0.5% (vol/vol) Triton™ X-100 for 30 min at room temperature, and stained overnight at 4° C. using Alexa Fluor® 488 phalloidin. Plugs were then washed three times using PBS and imaged on a confocal microscope (LSM780; Zeiss®). Serial optical sections were captured every 15 mm using a 20 objective lens. Individual confocal images are presented in sequence with increasing penetrance from left to right. Invasion was quantified using the area calculator plugin in ImageJ, measuring the fluorescence intensity of cells invading 45 mm or more and expressing this as a percentage of the fluorescence intensity of all cells within the plug. FIGS. 4B, 4C and 5 illustrate the results of inverted invasion assays. FIG. 4B shows examination of cell invasive ability in different head and neck cancer cell lines. The distance of migration >45 μm is set as cell invasion in inverted invasion assay. FIG. 4C shows depletion of LIMA1 inhibited cell invasion in UT-SCC-14, UT-SCC-45 and UT-SCC-60B cells. FIG. 5 shows depletion of LIMA1 attenuated cell invasion in breast cancer (BC) cells (Hs578T). Silencing of EPLIN caused a dramatic decrease in inverted invasion by the cancerous cell lines. Thus, EPLIN expression is demonstrated to be a factor in HNSCC and BC invasion and aggressiveness, and is a biomarker for aggressive cancer in both HNSCC and BC.

EPLIN-based Method in Personalized Referral to Treatment

Epidermal growth factor receptor (EGFR) is known to have a significant role in regulation of cancer invasiveness and aggressiveness, and target therapy drugs have been developed against EGFR. EGFR inhibitor (EGFRi) drugs are new generation cancer drugs which have a direct effect on EGFR function. However, it remains challenging to identify patients to whom administering EGFRi drugs provides efficient treatment. By our studies aimed at determining regulation between EPLIN and EGFR, we have now shown that EPLIN and EGFR interact in HNSCC cell lines. In our immunoprecipitation and mass spectrometry (MS) experiments with a commercial HNSCC cell line (FaDu) we could demonstrate that LIMA-1 interacted very strongly with epidermal growth factor receptor (EGFR) protein (FIG. 6A). Overexpression of LIMA-1 was achieved by Flag-EPLIN-b and detection of LIMA1 in immunoprecipitation (IP) was performed with Flag antibody (Invitrogen™). This result suggests that LIMA-1 and EGFR are tightly interacted in HNSCC. Moreover, silencing EPLIN (siEPLIN) with siRNA silencing reduces activity of EGFR protein after epidermal growth factor (EGF) stimulation in the breast cancer cell line MDA-MB-468 (FIG. 6B). The amount of active EGFR as detected by pY1068-EGFR is clearly decreased by siEPLIN. Silencing EPLIN also decreases the sensitivity of HNSCC cell lines to the EGFRi drugs EGFR tyrosine kinase inhibitors (EGFR-TKi) (FIG. 6C). The EGFR-TKis tested were Erlotinib, AZD9291, Afatinib, Cetuximab, AZD8931, Gefitinib and Neratinib. Of these, Erlotinib gave the best result (FIG. 6C).

Figure 7:
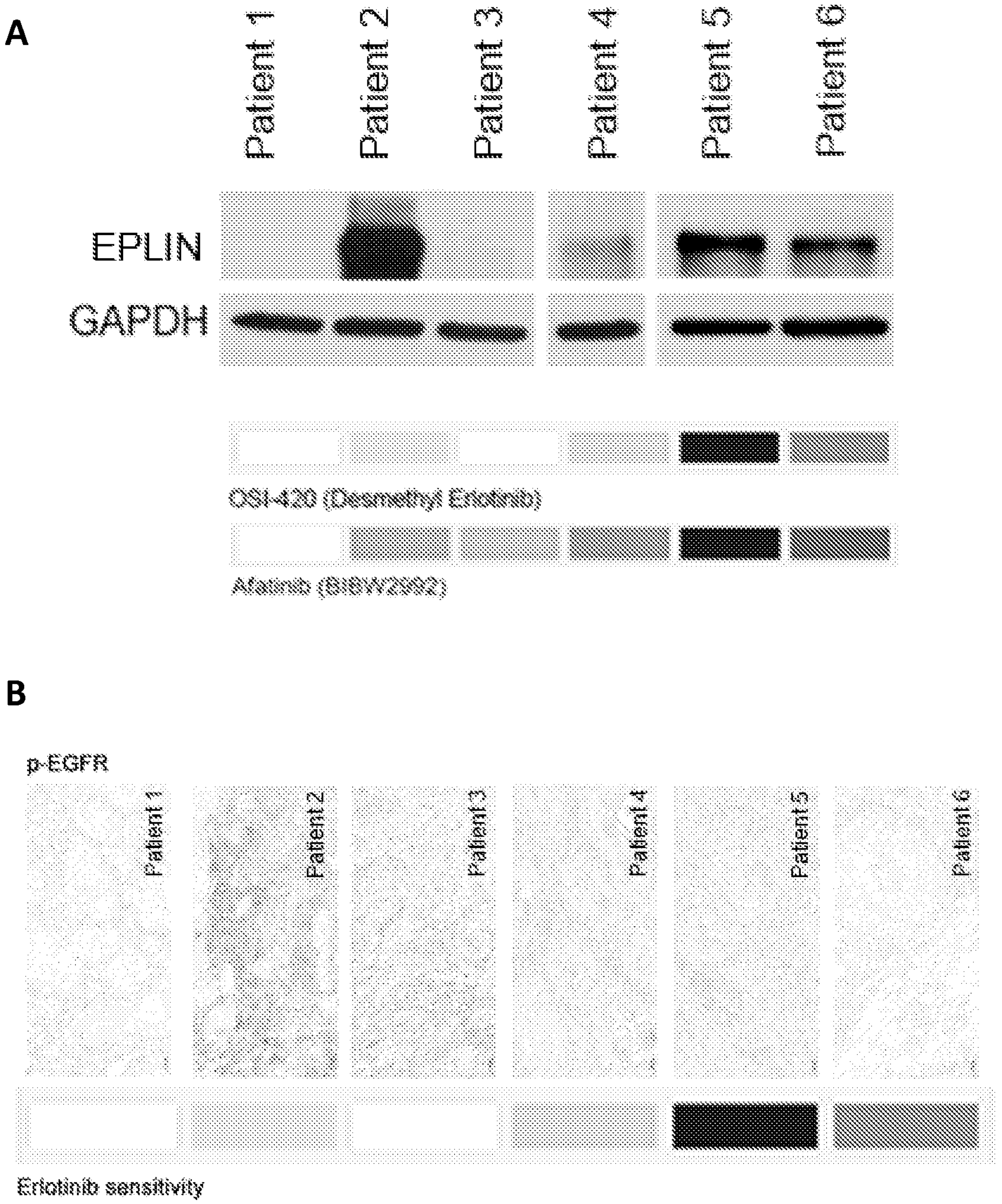
FIG. 7 illustrates selected results from a proof-of-concept study testing the sensitivity of more than 160 cancer drugs on nonselected HNSCC patient samples. EPLIN positive cancers were shown in the study to have high sensitivity to several EGFRi drugs and results of Erlotinib and Afatinib are shown in FIG. 7A as examples of this effect. Thus, EGFRis represent target therapy drugs in EPLIN positive HNSCC cancer cell lines. EPLIN protein expression analysis predicted sensitivity to EGFRi drugs even better than EGFR expression itself (FIG. 7B).

The results presented herein show that an EPLIN-based protein expression analysis can be used in identifying the cancer samples and cancer patients which are particularly sensitive to EGFRi group cancer drugs. Our proof-of-concept study featured testing the sensitivity of more than 160 cancer drugs on nonselected HNSCC patient samples using an internationally validated method (Misvik Oy, Turku, Finland). As a result it was shown that EGFRi drugs are highly effective cancer medicaments in EPLIN-positive cancers. FIG. 7 presents a selection of results obtained in this study. A high EPLIN expression was shown to correlate with an increased EGFRi sensitivity. EGFRi drugs Erlotinib, Gefitinib, Canertinib and Afatinib were shown in the study to have the highest sensitivity (all results not shown), and thus they represent target therapy drugs in EPLIN positive HNSCC cancer cell lines. Particularly, Erlotinib and Afatinib were proven to function as precision therapy on several EPLIN positive HNSCC patients (FIG. 7A). EPLIN expression analysis predicted sensitivity to EGFRi drugs even better than EGFR expression itself (FIG. 7B). Unlike with EPLIN, the patient samples that stained most intensely for EGFR were not the same as those that had highest EGFRi sensitivity.

It will be obvious to a person skilled in the art that, as the technology advances, the inventive concept can be implemented in various ways. The invention and its embodiments are not limited to the examples described above but may vary within the scope of the claims.

REFERENCES

Jacquemet G, et al. L-type calcium channels regulate filopodia stability and cancer cell invasion downstream of integrin signalling. Nat Commun 7, 13297 (2016). https://doi.org/10.1038/ncomms13297

Lepikhova T, et al. Drug-Sensitivity Screening and Genomic Characterization of 45 HPV-Negative Head and Neck Carcinoma Cell Lines for Novel Biomarkers of Drug Efficacy. Mol Cancer Ther. 2018 September; 17 (9):2060-2071. doi: 10.1158/1535-7163.MCT-17-0733.

Taha M, et al. EPLIN-α and -β Isoforms Modulate Endothelial Cell Dynamics through a Spatiotemporally Differentiated Interaction with Actin. Cell Rep. 2019 Oct. 22; 29 (4):1010-1026.e6. doi: 10.1016/j.celrep.2019.09.043.

The invention claimed is:

1. A method of treating HNSCC cancer in a subject, the method comprising:

a) assaying a HNSCC sample obtained from said subject for expression level of EPLIN, b) selecting as a treatment either:

(i) monotherapy with surgery when the expression of EPLIN is non-increased or decreased as compared to a relevant control level; or (ii) chemotherapy in combination with dissection, radiotherapy, or both dissection and radiotherapy, when the expression of EPLIN is increased as compared to the relevant control level; and c) administering the selected treatment to the subject.

2. The method of claim 1, wherein the relevant control level is the expression level of EPLIN in a non-diseased normal control or the relevant control level is determined from a sample collected from said subject treated for cancer before the treatment.

3. The method according to claim 1, wherein the chemotherapy is chemotherapy with an EGFR inhibitor being one or more selected from Erlotinib, AZD9291, Afatinib, Cetuximab, AZD8931, Gefitinib and Neratinib.

4. The method according to claim 1, wherein the cancer is T1/T2N0 and/or I/II cancer.

5. The method according to claim 1, wherein a sample is obtained from the cancer tumor and the healthy tissue area adjacent to the tumor, and expression level of EPLIN is determined from both samples.

6. The method according to claim 1, wherein the expression level of EPLIN is determined at mRNA, cDNA, or protein level.

7. The method according to claim 1, wherein the method comprises the use of a kit comprising one or more reagents that specifically detect EPLIN.

8. The method according to claim 1, wherein EPLIN is assayed as expression level of total EPLIN, EPLIN alpha or EPLIN beta or any combination thereof.

9. The method according to claim 1, wherein the expression level of total EPLIN and EPLIN alpha or EPLIN beta is assayed to determine a ratio between total EPLIN and EPLIN alpha or EPLIN beta.

* * * * *